(12) United States Patent
Holm

(10) Patent No.: US 7,994,214 B2
(45) Date of Patent: *Aug. 9, 2011

(54) SOLID DISPERSIONS COMPRISING TACROLIMUS

(75) Inventor: Per Holm, Vanlose (DK)

(73) Assignee: Lifecycle Pharma A/S, Horsholm (DK)

( * ) Notice: Subject to any disclaimer, the term of this patent is extended or adjusted under 35 U.S.C. 154(b) by 0 days.

This patent is subject to a terminal disclaimer.

(21) Appl. No.: 10/569,863

(22) PCT Filed: Aug. 30, 2004

(86) PCT No.: PCT/DK2004/000574
§ 371 (c)(1),
(2), (4) Date: Jun. 13, 2006

(87) PCT Pub. No.: WO2005/020994
PCT Pub. Date: Mar. 10, 2005

(65) Prior Publication Data
US 2010/0008984 A1    Jan. 14, 2010

Related U.S. Application Data

(60) Provisional application No. 60/529,793, filed on Dec. 15, 2003.

(30) Foreign Application Priority Data

| Aug. 29, 2003 | (DK) | ................................. | 2003 01232 |
| Dec. 11, 2003 | (DK) | ................................. | 2003 01837 |
| Jan. 21, 2004 | (DK) | ................................. | 2004 00079 |
| Mar. 23, 2004 | (DK) | ................................. | 2004 00463 |
| Mar. 23, 2004 | (DK) | ................................. | 2004 00467 |

(51) Int. Cl.
*A61K 31/435* (2006.01)
*A61K 9/22* (2006.01)
*A61K 9/26* (2006.01)

(52) U.S. Cl. ........ 514/450; 514/454; 514/338; 514/294; 514/885; 424/465; 424/468; 424/469

(58) Field of Classification Search .................. None
See application file for complete search history.

(56) References Cited

U.S. PATENT DOCUMENTS

| 5,601,844 | A | 2/1997 | Kagayama et al. |
| 6,168,806 | B1 * | 1/2001 | Lee et al. |
| 6,204,243 | B1 | 3/2001 | Posanski |
| 6,346,537 | B1 | 2/2002 | Hata et al. |
| 6,387,918 | B1 | 5/2002 | Yamanaka et al. |
| 6,440,458 | B1 | 8/2002 | Yamashita et al. |
| 6,503,883 | B1 | 1/2003 | Posanski |
| 6,576,259 | B2 * | 6/2003 | Yamashita et al. ............ 424/468 |
| 6,761,895 | B2 | 7/2004 | Sawada et al. |
| 6,884,433 | B2 | 4/2005 | Yamashita et al. |
| 6,884,436 | B2 | 4/2005 | Kipp et al. |
| 2002/0028240 | A1 | 3/2002 | Sawada et al. |
| 2003/0180352 | A1 * | 9/2003 | Patel et al. ..................... 424/465 |
| 2005/0169993 | A1 | 8/2005 | Yamashita et al. |
| 2005/0249799 | A1 | 11/2005 | Jacob et al. |
| 2006/0045865 | A1 | 3/2006 | Jacob et al. |
| 2006/0159766 | A1 | 7/2006 | Jenkins et al. |
| 2006/0177500 | A1 | 8/2006 | Shin et al. |
| 2006/0210638 | A1 | 9/2006 | Liversidge et al. |
| 2007/0122482 | A1 | 5/2007 | Holm et al. |

FOREIGN PATENT DOCUMENTS

| EP | 0 184 162 | A2 | 6/1986 |
| EP | 0 444 659 | A2 | 9/1991 |
| EP | 1 064 942 | A1 | 1/2001 |
| EP | 1064942 | A1 | 1/2001 |
| EP | 1275373 | A1 | 1/2003 |
| EP | 1275381 | A1 | 1/2003 |
| JP | 62-277321 | A | 12/1987 |
| WO | 93/23022 | A1 | 11/1993 |
| WO | 98/24418 | A1 | 6/1998 |
| WO | 99/49863 | A1 | 10/1999 |
| WO | 0137808 | A1 | 5/2001 |
| WO | WO 01/37808 | A1 | 5/2001 |
| WO | 01/74359 | A1 | 10/2001 |
| WO | WO 01/95939 | | 12/2001 |
| WO | WO 03/004001 | A1 | 1/2003 |
| WO | 2005/004848 | | 1/2005 |

OTHER PUBLICATIONS

"Tacrolimus (Systemic)", Drugs.com, Aug. 1997, pp. 1-43 of 43, downloaded from "www.drugs.com/mmx/tacrolimus.html" on Oct. 5, 2009.*
Yang et al., International Journal of Pharmaceutics, 1992, vol. 86(2-3) pp. 247-257; Abstract only, p. 1 of 1.*
Kjaergaard et al., "Prilling—Multiple Core Encapsulation", GEA Process Engineering, Inc., GEA-Niro A/S R1, Aug. 2000, downloaded from http://www.niroinc.com/food_chemical/prilling_encapsulation.asp, pp. 1-10 of 10.*
Nishi et al., 2004, "The colon displays an absorptive capacity of Tacrolimus", Transplantation Proceedings, vol. 36, No. 2, pp. 364-366.
Nishi et al., 2004, "The expression of intestinal CYP3A4 in the Piglet Model", Transplantation Proceedings vol. 36, No. 2, pp. 361-363.
Sano et al., 2002, "Oral FK 506 blood levels . . . " Transplantation Proceedings vol. 34, No. 3, pp. 1050-1051.
Honbo et al., 1987, "The oral dosage form of FK-506", Transplantation Proceedings, vol. 19, No. 5 supplement 6, pp. 17-22.
Official Action for U.S. Appl. No. 10/569,862; mail date Oct. 23, 2009; 23 pages.
Office Action dated Jun. 7, 2010 in U.S. Appl. No. 10/569,862.

* cited by examiner

*Primary Examiner* — James Anderson
*Assistant Examiner* — Gregg Polansky
(74) *Attorney, Agent, or Firm* — Blank Rome LLP

(57) ABSTRACT

A pharmaceutical composition comprising tacrolimus (FK-506) dissolved and/or dispersed in a hydrophilic or water-miscible vehicle to form a solid dispersion or solid solution at ambient temperature have improved bioavailability.

45 Claims, No Drawings

SOLID DISPERSIONS COMPRISING TACROLIMUS

The present invention relates to a solid dispersion comprising tacrolimus or an analogue thereof and having enhanced bioavailability, more specifically a solid solution or dispersion of tacrolimus in a hydrophilic vehicle; a pharmaceutical composition comprising the solid solution or dispersion; and dosage forms comprising the solid solution or dispersion.

BACKGROUND OF THE INVENTION

Tacrolimus, also known as FK-506 or FR-900506, has the chemical tricyclic structure shown below:

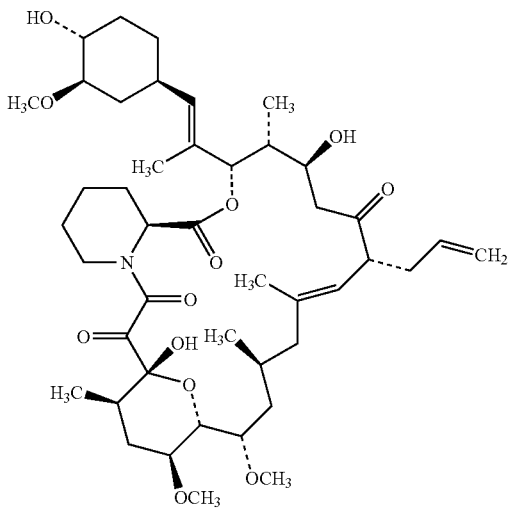

corresponding to $C_{44}H_{69}NO_{12}$. Tacrolimus appears in the form of white crystals or crystalline powder. It is practically insoluble in water, freely soluble in ethanol and very soluble in methanol and chloroform.

The preparation of tacrolimus is described in EP-A-0 184 162 and analogues of tacrolimus are disclosed e.g. in EP-A-0 444 659 and U.S. Pat. No. 6,387,918 (U.S. Pat. No. 6,387,918 is hereby incorporated by reference).

Tacrolimus is a macrolide compound with useful immunosuppressive activity, antimicrobial activity and other pharmacological activities and is of value for the treatment or prevention of rejection reactions by transplantation of organs or tissues, graft versus host diseases, autoimmune diseases and infectious diseases. Tacrolimus prolongs the survival of the host and transplanted graft in animal transplant models of liver, kidney, heart, bone marrow and small bowel and pancreas, lung and trachea, skin, cornea and limb.

In animals, tacrolimus has been demonstrated to suppress some humoral immunity and, to a greater extent, cell-mediated reactions such as allograft rejection, delayed type hypersensitivity, collagen-induced arthritis, experimental allergic encephalomyelitis and graft-versus-host disease.

Tacrolimus inhibits T-lymphocyte activation, although the exact mechanism of action is unknown. Experimental evidence suggest that tacrolimus binds to an intracellular protein, FKBP-12. A complex of tacrolimus-FKBP-12, calcium, calmodulin, and calcineurin is then formed and the phosphatase activity of calcineurin inhibited. This effect may prevent the dephosphorylation and translocation of nuclear factor of activated T-cells, a nuclear component thought to initiate gene transcription for the formation of lymphokines. The net result is the inhibition of T-lymphocyte activation, i.e. immunosuppression.

Tacrolimus is extensively metabolized by the CYP3A4 isoenzyme in the gut wall and liver. Therefore, drugs that affect this isoenzyme may influence absorption and the subsequent elimination of systemically absorbed tacrolimus. Inhibitors of CYP3A4 may increase tacrolimus levels, while inducers of CYP3A4 may increase the metabolism of tacrolimus and decrease tacrolimus levels. Accordingly, tacrolimus may be administered together with one or more CYP3A4 inhibitors in order to improve the overall bioavailability.

Usually tacrolimus is administered orally and is therefore absorbed from the gastrointestinal tract. It has been observed that the absorption is negatively influenced by the simultaneous ingestion of food. Thus, the rate and extent of tacrolimus absorption were greatest under fasted conditions.

In general, it is known that the absorption and bioavailability of a therapeutically active substance can be affected by a variety of factors when administered orally. Such factors include the presence of food in the gastrointestinal tract and, in general, the gastric residence time of a drug substance is significantly longer in the presence of food than in the fasted state. If the bioavailability of a drug substance is affected beyond a certain point due to the presence of food in the gastrointestinal tract, the drug substance is said to exhibit a food effect. Food effects are important because absorption and hence the plasma levels becomes highly variable depending on food intake. Absorption into the bloodstream may be adversely affected to the point that the patient risks insufficient absorption to remedy the condition for which the drug was administered. On the other hand, the very high peak concentrations seen at fasted conditions occasionally, may very well induce significant side effects, of nephro- or neurotoxic origin, as well as GI side-effects and others.

Absorption of tacrolimus from the gastrointestinal tract after oral administration is rapid with a mean time-to-peak concentration ($t_{max}$) of approximately 1-2 hours after administration to healthy subjects or kidney or liver transplanted patients, but incomplete and variable. The bioavailability is generally as low as at the most about 20% after oral administration.

Frequently observed side effects are vomiting and nausea but side effects like tremor, headache, hypertension, renal dysfunction, hyperkalemia, hypomagnesaemia, hyperglycemia, insomnia, diarrhea, constipation, abdominal pain, nephrotoxicity and neurotoxicity are also observed.

For oral administration, tacrolimus is currently formulated and marketed as soft gelatine capsules comprising the equivalent of 0.5, 1 or 5 mg anhydrous tacrolimus and marketed under the trade name Prograf® and Protropic®. The recommended initial oral dose is from about 0.1 to 0.2 mg/kg/day in patients. The dose aims at a certain trough plasma level from about 5 to about 20 ng/ml. Prograf® is indicated for the prophylaxis of organ rejection in patients receiving allogeneic liver or kidney transplants.

There remains a need for novel pharmaceutical compositions and/or dosage forms comprising tacrolimus exhibiting enhanced bioavailability. An increased bioavailability may allow a reduction in the dosage units taken by a patient, e.g. down to a single dose daily, and may also reduce or negate the need for food to be takes simultaneously with the dosage form thereby allowing patients more freedom on when the drug is taken. Furthermore, it is contemplated that fluctuations in the plasma concentration versus time profile may be significantly reduced. Further, enhanced bioavailability may also result in a more reproducible (i.e. less variable compared to that of Prograf®) release profile.

BRIEF SUMMARY OF THE INVENTION

The inventors have now found that the bioavailability of tacrolimus can be significantly enhanced by dispersing or dissolving tacrolimus in a hydrophilic or water-miscible vehicle in an amount which is efficient for use in the preparation of a useful drug dosage form. Tacrolimus is known to have a very low solubility in water, but this invention provides pharmaceutical compositions and formulations exhibiting very fast in vitro release profiles, i.e. immediate release compositions which are contemplated having significantly increased in vivo bioavailability in patients in need thereof.

Accordingly, in a first aspect the present invention relates to a solid dispersion comprising an active ingredient selected among tacrolimus and analogues thereof dispersed or dissolved in a hydrophilic or water-miscible vehicle, wherein the melting point of the vehicle is at least 20° C. and the active ingredient is present therein in a concentration of between about 0.01 w/w % and as much as up to about 15 w/w % to form a solid dispersion or solid solution at ambient temperature. It is believed, that this dispersion is capable of releasing at least 50 w/w % of the amount of tacrolimus within about 30 minutes, when tested in any dissolution test according to USP using an aqueous dissolution medium.

In a further aspect, the invention relates to a pharmaceutical composition comprising the solid dispersion and/or solution of tacrolimus and one or more pharmaceutically acceptable excipients, which may be fillers, disintegrants, binders or lubricants. In yet another aspect, the invention relates to dosage forms such as solid oral unit dosage forms comprising the solid dispersion and/or solution of tacrolimus, pharmaceutically acceptable excipients and optionally pharmaceutically acceptable additive such as flavoring agents, coloring agents, taste-masking agents, pH-adjusting agents, buffering agents, preservatives, stabilizing agents, anti-oxidants, wetting agents, humidity-adjusting agents, surface-active agents, suspending agents, absorption enhancing agents and release modifying agents. Especially, the present invention relates to a dosage form comprising tacrolimus and release-modifying agents, especially dosage forms having delayed release such as solid oral unit dosage forms including enteric coating. Delaying the release of tacrolimus to the distal part of duodenum may reduce the drug related gastro-intestinal related side effects and the relatively high degree of metabolism in the proximal part of the gastrointestinal tract (CYP3A4 mediated metabolism). Owing to the novel solid dispersion and/or solution according to this invention, this is done without loosing systemic bioavailability.

DETAILED DESCRIPTION OF THE INVENTION

Definitions

As used herein, the term "active ingredient" or "active pharmaceutical ingredient" means any component that is intended to furnish pharmacological activity or other direct effect in the diagnosis, cure, mitigation, treatment, or prevention of disease, or to affect the structure or any function of the body of man or other animals. The term includes those components that may undergo chemical change in the manufacture of the drug product and are present in the drug product in a modified form intended to furnish the specified activity or effect.

In the present context, the term "hydrophilic" describes that something 'likes water', i.e. a hydrophilic molecule or portion of a molecule is one that typically is electrically polarized and capable of forming hydrogen bonds with water molecules, enabling it dissolve more readily in water than in oil or other "non-polar" solvents.

In the present context, the term "amphiphilic" describes a molecule (as a surfactant) having a polar water-soluble group attached to a water-insoluble hydrocarbon chain. Thus, one end of the molecule is hydrophilic (polar) and the other is hydrophobic (non-polar).

As used herein, the term "vehicle" means any solvent or carrier fluid in a pharmaceutical product that has no pharmacological role. For example, water is the vehicle for xilocaine and propylene glycol is the vehicle for many antibiotics.

In the present context, the term "solid dispersion" denotes a drug or active ingredient or substance dispersed on a particulate level in an inert vehicle, carrier, diluent or matrix in the solid state, i.e. usually a fine particulate dispersion.

In the present context, the term "solid solution" denotes a drug or active ingredient or substance dissolved on a molecular level in an inert vehicle, carrier, diluent or matrix in the solid state.

As used herein, the term "analogue" means a chemical compound that is structurally similar to another.

The term "drug" means a compound intended for use in diagnosis, cure, mitigation, treatment, or prevention of disease in man or other animals.

In this context, the term "dosage form" means the form in which the drug is delivered to the patient. This could be parenteral, topical, tablet, oral (liquid or dissolved powder), suppository, inhalation, transdermal, etc.

As used herein, the term "bioavailability" denotes the degree means to which a drug or other substance becomes available to the target tissue after administration. As used herein, the term "bioequivalency" denotes a scientific basis on which generic and brand name drugs are compared with one another. For example, drugs are bioequivalent if they enter circulation at the same rate when given in similar doses under similar conditions. Parameters often used in bioequivalence studies are $t_{max}$, $c_{max}$, $AUC_{0-infinity}$, $AUC_{0-t}$. Other relevant parameters may be $W_{50}$, $W_{75}$ and/or MRT. Accordingly, at least one of these parameters may be applied when determining whether bioequivalence is present. Furthermore, in the present context, two compositions are regarded as bioequivalent if the value of the parameter used is within 80-125% of that of Prograf® or a similar commercially available tacrolimus-containing product used in the test.

In the present context "$t_{max}$" denotes the time to reach the maximal plasma concentration ($c_{max}$) after administration; $AUC_{0-infinity}$ denotes the area under the plasma concentration versus time curve from time 0 to infinity; $AUC_{0-t}$ denotes the area under the plasma concentration versus time curve from time 0 to time t; $W_{50}$ denotes the time where the plasma concentration is 50% or more of $C_{max}$; $W_{75}$ denotes the time where the plasma concentration is 75% or more of $C_{max}$; and MRT denotes mean residence time for tacrolimus (and/or an analogue thereof).

In this context, the term "medicine" means a compound used to treat disease, injury or pain. Medicine is justly distributed into "prophylactic," i.e. the art of preserving health, and "therapeutic", i.e. the art of restoring health.

As used herein, the term "delayed release" means a release profile of a drug from a pharmaceutical composition or formulation which, in relation to the immediate release profile, has an unchanged $C_{max}$, but simply a lag time from the time of administration until drug release. Accordingly, $t_{max}$, is delayed, and $t_{1/2}$ is usually unchanged.

In this context, the term "erosion" or "eroding" means a gradual breakdown of the surface of a material or structure, for example of a tablet or the coating of a tablet.

Solid Dispersion and/or Solid Solution of Tacrolimus

The solid dispersion of the invention comprises an active ingredient selected among tacrolimus and analogues thereof, which ingredient is dispersed or dissolved in a hydrophilic or water-miscible vehicle having a melting point (freezing point or pour point) of at least 20° C. in a concentration of between about 0.01 w/w % and about 15 w/w %, and which dispersion is forming a solid dispersion or solid solution at ambient temperature (room temperature).

The active ingredient is preferably tacrolimus or any analogue or derivative of tacrolimus, which exhibits either a pharmacological or a therapeutic activity, which is at least equivalent to that of tacrolimus (FK-506 or FR-900506). However, within the scope of the present invention is tacrolimus in any physical form (crystals, amorphous powder, any possible polymorphs, any possible solvates including the hydrate, anhydrate, complexes thereof etc.). Included is also any analogue, derivative or active metabolite of tacrolimus, pharmaceutically acceptable salts, solvates, complexes and prodrugs thereof.

The concentration of the active ingredient in the hydrophilic or water-miscible vehicle is at the most 15 w/w %, preferably at the most 10 w/w %, preferably at the most 8 w/w %, more preferably at the most 6 w/w %, even more preferably at the most 5 w/w %, at the most 4% w/w, especially at the most 3 w/w %, in particular at the most 2% w/w; and/or is at least about 0.05 w/w %, preferably at least about 0.1 w/w %, more preferably at least about 0.5 w/w %, especially at least about 0.7 w/w %, in particular at least about 1 w/w %.

Physically, the combination of active ingredient and vehicle may either form a solid dispersion, i.e. the active ingredient is dispersed in the vehicle in particulate form, or may form a solid solution, i.e. the active ingredient is dissolved in the vehicle at a molecular level. The active ingredient and the vehicle may also form a solid dispersion having therein a part of the active ingredient dissolved at a molecular level. The physical state of the dispersion and/or solution may be determined by using various techniques such as Hot Stage Microscopy (HSM), Differential Scanning Calorimetry (DSC), Scanning Electron Microscopy (SEM) optionally in combination with Energy Dispersive X-ray (EDX), and X-ray powder diffraction. In a preferred embodiment, the active ingredient is fully dissolved in the vehicle to form a solid solution at ambient temperature.

Increasing the bioavailability, the Area Under the Curve (AUC), will normally reduce the intra- and inter-variability related to absorption of a drug substance. This is particularly true; whenever the low and impaired bioavailability is a consequence of poor water solubility. It is contemplated that compositions according to the invention will provide a CV (Coefficient of Variation) on AUC data having a significantly lesser value than that of Prograf® and like products.

As mentioned hereinbefore, one of the basic features of the present invention is that it is possible to obtain an improvement in the bioavailability by oral administration of a composition of the present invention. Normally, a low bioavailability of a drug substance after oral administration is a barrier for design of a controlled or modified release composition of the drug substance due to the fact that it is almost impossible to obtain effective drug levels over a prolonged period of time. However, with the present technology it is possible to obtain a significantly improved bioavailability and thereby possible to design for example delayed release compositions.

The solid dispersion of the invention exhibits a very fast immediate release of tacrolimus, when a composition comprising the dispersion or solution is tested in a dissolution test according to USP using an aqueous dissolution medium, and at least 50 w/w % of the active pharmaceutical ingredient is released within about 30 minutes, preferably within 20 minutes, more preferably within 15 minutes; such as at least 75 w/w % of the active pharmaceutical ingredient is released within about 40 minutes, or even better at least 90 w/w % of the active pharmaceutical ingredient is released within about 60 minutes, preferably within 45 minutes. For example, the test may be carried out according to the any method and any specifications cited in USP. Thus, the dissolution test may be carried out in an aqueous dissolution medium at a neutral or near-neutral pH, for example at pH 6.8, or at any acidic pH simulating the pH conditions in the gastrointestinal tract. However, variations with respect to the specific method employed and the ingredients contained in the dissolution medium etc. are within the scope of the present invention. A person skilled in the art will know how to carry out a suitable dissolution test e.g. with guidance from USP, Ph. Eur. and the like. Suitable conditions for the in vitro dissolution test are employing USP dissolution test (paddle method) and a buffer pH 7.5 containing 2.5% SDS and 1 g/mL of pancreatin as dissolution medium.

In other embodiments, the following conditions are fulfilled with respect to in vitro dissolution tests:
i) at least about 50% w/w of the total amount of tacrolimus or an analogue thereof is released within about 10 hours such as, e.g., within about 8 hours, within about 6 hours, within about 4 hours, within about 3 hours, within about 2 hours, within about 1 hour, within about 45 min, within about 30 min or within about 15 min, when tested in an in vitro dissolution test and employing a dissolution medium comprising a buffer having pH 7.5
ii) at least about 50% w/w of the total amount of tacrolimus or an analogue thereof is released within about 1.5 hours such as, e.g., within about 1 hour, within about 0.75 hours, within about 0.5 hours or within about 20 minutes, when tested in an in vitro dissolution test and employing a dissolution medium comprising a buffer having pH 7.5.
iii) at least about 55% w/w such as, e.g., about 60% w/w or more, about 65% w/w or more, about 70% w/w or more, about 75% w/w or more or about 80% w/w or more of the total amount of tacrolimus or an analogue thereof is released within about 15 hours such as, e.g., within about 12 hours, within about 10 hours, within 8 hours or within about 6 hours, when tested in an in vitro dissolution test and employing a dissolution medium comprising a buffer having pH 7.5
iv) at least about 55% w/w such as, e.g., about 60% w/w or more, about 65% w/w or more, about 70% w/w or more, about 75% w/w or more or about 80% w/w or more of the total amount of tacrolimus or an analogue thereof is released within about 5 hours such as, e.g., within about 4 hours, within about 3 hours, within about 2 hours, within about 1 hours or within about 30 minutes, when tested in an in vitro dissolution test and employing a dissolution medium comprising a buffer having pH 7.5, and/or
v) at least about 20% w/w such as, e.g., at least about 25% w/w, at least about 30% w/w, at least about 35% w/w or at least about 40% w/w of the total amount of tacrolimus or an analogue thereof is released within the first 3 hours such as, e.g., within the first 2 hours or within the first hour when tested in an in vitro dissolution test and employing a dissolution medium comprising a buffer having pH 7.5.

In other embodiments of the invention, the following conditions are fulfilled with respect to in vitro dissolution tests performed under acidic conditions:

i) at the most about 30% w/w such as, e.g., at the most about 25% w/w, at the most about 20% w/w, at the most about 15% w/w or at the most about 10% w/w of tacrolimus or an analogue thereof is released within 2 hours in an in vitro dissolution test employing a dissolution medium having a pH of at the most about 5 such as, e.g. at the most about 4.5, at the most about 4, at the most about 3.5, at the most about 3, at the most about 2 or at the most about 1.5;

ii) at the most about 10% w/w such as, e.g., at the most about 7.5% w/w, at the most about 5% w/w or at the most about 2.5% w/w of tacrolimus or an analogue thereof is released within 2 hours in an in vitro dissolution test employing a dissolution medium having a pH of at the most about 5 such as, e.g. at the most about 4.5, at the most about 4, at the most about 3.5, at the most about 3, at the most about 2 or at the most about 1.5;

iii) at the most about 60% w/w such as, e.g., at the most about 50% w/w, at the most about 40% w/w or at the most about 30% w/w of tacrolimus or an analogue thereof is released within 15 hours such as, e.g., within about 12 hours, when tested in an in vitro dissolution test employing a dissolution medium having a pH of at the most about 4.5 such as, e.g. at the most about 4.0, at the most about 3.5, at the most about 3, at the most about 2 or at the most about 1.5;

iv) at the most about 40% w/w such as, e.g., at the most about 30% w/w, at the most about 25% w/w or at the most about 20% w/w of tacrolimus or an analogue thereof is released within 6 hours when tested in an in vitro dissolution test employing a dissolution medium having a pH of at the most about 4.5 such as, e.g. at the most about 4.0, at the most about 3.5, at the most about 3, at the most about 2 or at the most about 1.5, and/or v) at the most about 30% w/w such as, e.g., at the most about 25% w/w, at the most about 20% w/w or at the most about 15% w/w of tacrolimus or an analogue thereof is released within 4 hours when tested in an in vitro dissolution test employing a dissolution medium having a pH of at the most about 4.5 such as, e.g. at the most about 4.0, at the most about 3.5, at the most about 3, at the most about 2 or at the most about 1.5.

The hydrophilic or water-miscible vehicle to be used according to the invention is preferably one having a melting point (freezing point or pour point) of at least 20° C., more preferably at least 30° C., more preferably at least 40° C., more preferably at least 50° C., even more preferably at least 52° C., even more preferably at least 55° C., even more preferably at least 59° C., especially at least 61° C., in particular at least 65° C.

Examples of useful hydrophilic or water-miscible vehicles to be used according to this invention are selected from the group consisting of polyethylene glycols, polyoxyethylene oxides, poloxamers, polyoxyethylene stearates, poly-epsilon caprolactone, polyglycolized glycerides such as Gelucire®, and mixtures thereof.

It is also contemplated that certain amphiphilic vehicles may be useful in the present invention, including those vehicles disclosed herein which may be amphiphilic in addition to being water-miscible.

In a preferred embodiment of the invention, the vehicle is a polyethylene glycol (PEG), in particular a PEG having an average molecular weight of at least 1500, preferably at least 3000, more preferably at least 4000, especially at least 6000. The polyethylene glycol may advantageously be mixed with one or more other hydrophilic or water-miscible vehicles, for example a poloxamer, preferably in a proportion (on a weight/weight basis) of between 1:3 and 10:1, preferably between 1:1 and 5:1, more preferably between and 3:2 4:1, especially between 2:1 and 3:1, in particular about 7:3. A specific example of a useful mixture is a mixture of PEG6000 and poloxamer 188 in the ratio 7:3.

For polyethylene glycols (PEG), the melting point (freezing point or pour point) increases as the average molecular weight increases. For example, PEG 400 is in the range of 4-8° C., PEG 600 is in the range of 20-25° C., PEG1500 is in the range of 44-48° C., PEG2000 is about 52° C., PEG 4000 is about 59° C., PEG 6000 is about 65° C. and PEG 8000 is about 61° C.

Useful poloxamers (also denoted polyoxypropylene-polyoxyethylene block copolymers) are for example poloxamer 188, poloxamer 237, poloxamer 338 or poloxamer 407 or other block copolymers of ethylene oxide and propylene oxide such as the Pluronic® and/or Tetronic® series. Suitable block copolymers of the Pluronic® series include polymers having a molecular weight of about 3,000 or more such as, e.g. from about 4,000 to about 20,000 and/or a viscosity (Brookfield) from about 200 to about 4,000 cps such as, e.g., from about 250 to about 3,000 cps. Suitable examples include Pluronic® F38, P65, P68LF, P75, F77, P84, P85, F87, F88, F98, P103, P104, P105, F108, P123, F123, F127, 10R8, 17R8, 25R5, 25R8 etc. Suitable block copolymers of the Tetronic® series include polymers having a molecular weight of about 8,000 or more such as, e.g., from about 9,000 to about 35,000 and/or a viscosity (Brookfield) of from about 500 to about 45,000 cps such as, e.g., from about 600 to about 40,000. The viscosities given above are determined at 60° C. for substances that are pastes at room temperature and at 77° C. for substances that are solids at room temperature.

In a preferred embodiment of the present invention, the poloxamer is poloxamer 188, which has an average molecular weight of about 8400 and a melting point of about 50-54° C.

Other useful hydrophilic or water-miscible vehicles may be polyvinylpyrrolidones, polyvinyl-polyvinylacetate copolymers (PVP-PVA), polyvinyl alcohol (PVA), polymethacrylic polymers (Eudragit® RS; Eudragit® RL, Eudragit® NE, Eudragit® E), cellulose derivatives including hydroxypropyl methylcellulose (HPMC), hydroxypropyl cellulose (HPC), methylcellulose, sodium carboxymethylcellulose, hydroxyethyl cellulose, pectins, cyclodextrins, galactomannans, alginates, carragenates, xanthan gums and mixtures thereof.

"Polyglycolized glycerides" denotes a mixture of mono-, di- and triglycerides and polyethylene glycol (PEG) mono- and diesters, preferably of molecular weight between 200 and 600, where appropriate of free glycerol and free PEG, whose HLB value is adjusted by the length of the PEG chain, and whose melting point is adjusted by the length of the chains of the fatty acids, of the PEG and by the degree of saturation of the fatty chains, and hence of the starting oil; examples of such mixtures are Gelucire®. Gelucire® compositions are inert semi-solid waxy materials which are amphiphilic in character and are available with varying physical characteristics. They are surface active in nature and disperse or solubilize in aqueous media forming micelles, microscopic globules or vesicles. They are identified by their melting point/HLB value. The melting point is expressed in degrees Celsius and the HLB (Hydrophile-Lipophile Balance) is a numerical scale extending from 0 to approximately 20. Lower HLB values denote more lipophilic and hydrophobic substances, and higher values denote more hydrophilic and lipophobic substances. The affinity of a compound for water or for oily substances is determined and its HLB value is assigned experimentally. One or a mixture of different grades of Gelucire® excipient may be chosen to achieve the desired characteristics of melting point and/or HLB value. They are mixtures of monoesters, diesters and/or triesters of glycerides of long chain ($C_{12}$ to $C_{18}$) fatty acids, and PEG (mono- and/or di) esters of long chain ($C_{12}$ to $C_{18}$) fatty acids and can include free PEG. Gelucire® compositions are generally described as fatty acid esters of glycerol and PEG esters or as polyglycolized glycerides. Gelucire® compositions are characterized by a wide range of melting points of from about 33° C. to about 64° C. and most commonly from about 35° C. to about 55° C., and by a variety of HLB values of from about 1 to about 14, most commonly from about 7 to about 14. For example, Gelucire® 50/13 designates a melting point of approximately 50° C. and an HLB value of about 13 to this grade of Gelucire®.

Pharmaceutical Compositions

The pharmaceutical composition of the invention comprises the solid dispersion or solid solution of the invention and one or more pharmaceutically acceptable excipients, for example one or more excipients useful as fillers, disintegrants, binders and/or lubricants.

Preferably, the pharmaceutical composition of the invention is in particulate form, for example in powder form. Preferably, the particulate material obtained is a free-flowing powder and therefore readily processable into e.g. solid dosage forms such as tablets, capsules or sachets. Normally, the particulate material has properties that are suitable in order to manufacture tablets by direct compression without addition of large amounts of further additives. A suitable test for testing the flowability of the particulate material is the method described in Ph. Eur. and measuring the flow rate of the material out of a funnel with a nozzle (orifice) diameter of 10.0 mm.

The particles may have a geometric weight mean diameter $d_{gw}$ from about 10 μm to about 2000 μm, preferably from about 20 μm to about 2000 μm, more preferably from about 30 μm to about 2000 μm, more preferably from about 50 μm to about 2000 μm, more preferably from about 60 μm to about 2000 μm, more preferably from about 75 μm to about 2000 μm, more preferably from about 100 μm to about 1500 μm, more preferably from about 100 μm to about 1000 μm, more preferably from about 100 μm to about 700 μm, more preferably from about 50 μm to about 400 μm, more preferably from about 50 μm to about 350 μm, even more preferably from about 50 μm to about 300 μm, especially from about 50 μm to about 250 μm or, in particular, from about 100 μm to about 300 μm. In a preferred embodiment of the invention, the particles have a geometric weight mean diameter $d_{gw}$ from about 50 μm to about 300 μm.

Examples on suitable excipients for use in a composition or solid dosage form according to the invention include fillers, diluents, disintegrants, binders, lubricants etc. or mixture thereof. As the composition or solid dosage form according to the invention may be used for different purposes, the choice of excipients is normally made taken such different uses into considerations. Other pharmaceutically acceptable excipients for suitable use are e.g. acidifying agents, alkalizing agents, preservatives, antioxidants, buffering agents, chelating agents, coloring agents, complexing agents, emulsifying and/or solubilizing agents, flavors and perfumes, humectants, sweetening agents, wetting agents etc.

Examples on suitable fillers, diluents and/or binders include lactose (e.g. spray-dried lactose, α-lactose, β-lactose, Tabletose®, various grades of Pharmatose®, Microtose®; or Fast-Floc®, microcrystalline cellulose (various grades of Avicel®, Elcema®, Vivacel®, Ming Tai® or Solka-Floc®), hydroxypropylcellulose, L-hydroxypropylcellulose (low substituted), hydroxypropyl methylcellulose (HPMC) (e.g. Methocel® E, F and K, Metolose® SH of Shin-Etsu, Ltd, such as, e.g. the 4,000 cps grades of Methocel E and Metolose® 60 SH, the 4,000 cps grades of Methocel® F and Metolose® 65 SH, the 4,000, 15,000 and 100,000 cps grades of Methocel® K; and the 4,000, 15,000, 39,000 and 100,000 grades of Metolose® 90 SH), methylcellulose polymers (such as, e.g., Methocel® A, Methocel® A4C, Methocel® A15C, Methocel® A4M), hydroxyethylcellulose, sodium carboxymethylcellulose, carboxymethylene, carboxymethylhydroxyethylcellulose and other cellulose derivatives, sucrose, agarose, sorbitol, mannitol, dextrins, maltodextrins, starches or modified starches (including potato starch, maize starch and rice starch), calcium phosphate (e.g. basic calcium phosphate, calcium hydrogen phosphate, dicalcium phosphate hydrate), calcium sulfate, calcium carbonate, sodium alginate, collagen etc.

Specific examples of diluents are e.g. calcium carbonate, dibasic calcium phosphate, tribasic calcium phosphate, calcium sulfate, microcrystalline cellulose, powdered cellulose, dextrans, dextrin, dextrose, fructose, kaolin, lactose, mannitol, sorbitol, starch, pregelatinized starch, sucrose, sugar etc.

Specific examples of disintegrants are e.g. alginic acid or alginates, microcrystalline cellulose, hydroxypropyl cellulose and other cellulose derivatives, croscarmellose sodium, crospovidone, polacrillin potassium, sodium starch glycolate, starch, pregelatinized starch, carboxymethyl starch (e.g. Primogel® and Explotab®) etc.

Specific examples of binders are e.g. acacia, alginic acid, agar, calcium carrageenan, sodium carboxymethylcellulose, microcrystalline cellulose, dextrin, ethylcellulose, gelatin, liquid glucose, guar gum, hydroxypropyl methylcellulose, methylcellulose, pectin, PEG, povidone, pregelatinized starch etc.

Glidants and lubricants may also be included in the composition. Examples include stearic acid, magnesium stearate, calcium stearate or other metallic stearate, talc, waxes and glycerides, light mineral oil, PEG, glyceryl behenate, colloidal silica, hydrogenated vegetable oils, corn starch, sodium stearyl fumarate, polyethylene glycols, alkyl sulfates, sodium benzoate, sodium acetate etc.

Other excipients which may be included in a composition or solid dosage form of the invention are e.g. flavoring agents, coloring agents, taste-masking agents, pH-adjusting agents, buffering agents, preservatives, stabilizing agents, anti-oxidants, wetting agents, humidity-adjusting agents, surface-active agents, suspending agents, absorption enhancing agents, agents for modified release etc.

Other additives in a composition or a solid dosage form according to the invention may be antioxidants like e.g. ascorbic acid, ascorbyl palmitate, butylated hydroxyanisole, butylated hydroxytoluene, hypophosphorous acid, monothioglycerol, potassium metabisulfite, propyl gallate, sodium formaldehyde sulfoxylate, sodium metabisulfite, sodium thiosulfate, sulfur dioxide, tocopherol, tocopherol acetate, tocopherol hemisuccinate, TPGS or other tocopherol derivatives, etc. The carrier composition may also contain e.g. stabilising agents. The concentration of an antioxidant and/or a stabilizing agent in the carrier composition is normally from about 0.1% w/w to about 5% w/w.

The pharmaceutical composition or solid dosage form according to the invention may also include one or more surfactants or substances having surface-active properties. It is contemplated that such substances are involved in the wetting of the slightly soluble active substance and thus, contributes to improved solubility characteristics of the active substance. Suitable excipients for use in a composition or a solid dosage form according to the invention are surfactants such as, e.g., amphiphilic surfactants as those disclosed in WO 00/50007 in the name of Lipocine, Inc.

Examples of suitable substances useful as surfactants and or even as vehicles are i) polyethoxylated fatty acids such as, e.g. fatty acid mono- or diesters of polyethylene glycol or mixtures thereof such as, e.g. mono- or diesters of polyethylene glycol with lauric acid, oleic acid, stearic acid, myristic acid, ricinoleic acid, and the polyethylene glycol may be selected from PEG 4, PEG 5, PEG 6, PEG 7, PEG 8, PEG 9, PEG 10, PEG 12, PEG 15, PEG 20, PEG 25, PEG 30, PEG 32, PEG 40, PEG 45, PEG 50, PEG 55, PEG 100, PEG 200, PEG 400, PEG 600, PEG 800, PEG 1000, PEG 2000, PEG 3000, PEG 4000, PEG 5000, PEG 6000, PEG 7000, PEG 8000, PEG 9000, PEG 1000, PEG 10,000, PEG 15,000, PEG 20,000, PEG 35,000, ii) polyethylene glycol glycerol fatty acid esters, i.e. esters like the above-mentioned but in the form of glyceryl esters of the individual fatty acids;

iii) glycerol, propylene glycol, ethylene glycol, PEG or sorbitol esters with e.g. vegetable oils like e.g. hydrogenated castor oil, almond oil, palm kernel oil, castor oil, apricot kernel oil, olive oil, peanut oil, hydrogenated palm kernel oil and the like, iv) polyglycerized fatty acids like e.g. polyglycerol stearate, polyglycerol oleate, polyglycerol ricinoleate, polyglycerol linoleate, v) propylene glycol fatty acid esters such as, e.g. propylene glycol monolaurate, propylene glycol ricinoleate and the like, vi) mono- and diglycerides like e.g. glyceryl monooleate, glyceryl dioleae, glyceryl mono- and/or dioleate, glyceryl caprylate, glyceryl caprate etc.;

vii) sterol and sterol derivatives;

viii) polyethylene glycol sorbitan fatty acid esters (PEG-sorbitan fatty acid esters) such as esters of PEG with the various molecular weights indicated above, and the various Tween® series;

ix) polyethylene glycol alkyl ethers such as, e.g. PEG oleyl ether and PEG lauryl ether;

x) sugar esters like e.g. sucrose monopalmitate and sucrose monolaurate;

xi) polyethylene glycol alkyl phenols like e.g. the Triton® X or N series;

xii) polyoxyethylene-polyoxypropylene block copolymers such as, e.g., the Pluronic® series, the Synperonic® series, Emkalyx®, Lutrol®, Supronic®) etc. The generic term for these polymers is "poloxamers" and relevant examples in the present context are Poloxamer 105, 108, 122, 123, 124, 181, 182, 183, 184, 185, 188, 212, 215, 217, 231, 234, 235, 237, 238, 282, 284, 288, 331, 333, 334, 335, 338, 401, 402, 403 and 407;

xiii) sorbitan fatty acid esters like the Span® series or Ariacel® series such as, e.g. sorbinan monolaurate, sorbitan monopalmitate, sorbitan monooleate, sorbitan monostearate etc.;

xiv) lower alcohol fatty acid esters like e.g. oleate, isopropyl myristate, isopropyl palmitate etc.;

xv) ionic surfactants including cationic, anionic and zwitterionic surfactants such as, e.g. fatty acid salts, bile salts, phospholipids, phosphoric acid esters, carboxylates, sulfates and sulfonates etc.

When a surfactant or a mixture of surfactants is present in a composition or a solid dosage form of the invention, the concentration of the surfactant(s) is normally in a range of from about 0.1-80% w/w such as, e.g., from about 0.1 to about 20% w/w, from about 0.1 to about 15% w/w, from about 0.5 to about 10% w/w, or alternatively, from about 0.10 to about 80% w/w such as, e.g. from about 10 to about 70% w/w, from about 20 to about 60% w/w or from about 30 to about 50% w/w.

In a specific aspect of the invention, the at least one of the one or more pharmaceutically acceptable excipient is selected from the group consisting of silica acid or a derivative or salt thereof including silicates, silicon dioxide and polymers thereof; magnesium aluminosilicate and/or magnesium aluminometasilicate, bentonite, kaolin, magnesium trisilicate, montmorillonite and/or saponite.

Such materials are is especially useful as a sorption material for oils or oily materials in pharmaceuticals, cosmetics and/or foodstuff. In a specific embodiment, the material is used as a sorption material for oils or oily materials in pharmaceuticals. The material that has the ability to function as a sorption material for oils or oily materials is also denoted "oil sorption material". Furthermore, in the present context the term "sorption" is used to denote "absorption" as well as "adsorption". It should be understood that whenever one of the terms is used it is intended to cover the phenomenon absorption as well as adsorption.

Notably, the pharmaceutically acceptable excipient may comprise a silica acid or a derivative or salt thereof such as, e.g., silicon dioxide or a polymer thereof as a pharmaceutically acceptable excipient. Dependent on the quality employed a silicon dioxide may be a lubricant or it may be an oil sorption material. Qualities fulfilling the latter function seem to be most important.

In a specific embodiment, the composition or solid dosage form according to invention comprises a pharmaceutically acceptable excipient that is a silicon dioxide product that has properties corresponding to Aeroperl® 300 (available from Degussa, Frankfurt, Germany).

As it appears from the examples herein, a very suitable material is Aeroperl® 300 (including materials with properties like or corresponding to those of Aeroperl® 300).

Use of an oil sorption material in compositions or dosage forms according to the invention is very advantageous for the preparation of pharmaceutical, cosmetic, nutritional and/or food compositions, wherein the composition comprises oil or an oily material. One of the advantages is that is it possible to incorporate a relatively large amount of oil and oily material and still have a material that is solid. Thus, it is possible to prepare solid compositions with a relatively high load of oil or oily materials by use of an oil sorption material according to the invention. Within the pharmaceutical field it is an advantage to be able to incorporate a relatively large amount of an oil or an oily-like material in a solid composition especially in those situation where the active substance does not have suitable properties with respect to water solubility (e.g. poor water solubility), stability in aqueous medium (i.e. degradation occurs in aqueous medium), oral bioavailability (e.g. low bioavailability) etc., or in those situations where it is desired to modify the release of an active substance from a composition in order to obtain a controlled, delayed, sustained and/or pulsed delivery of the active substance. Thus, in a specific embodiment it is used in the preparation of pharmaceutical compositions.

The oil sorption material for use in the processing into solid compositions normally absorbs about 5% w/w or more, such as, e.g., about 10% w/w or more, about 15% w/w or more, about 20% w/w or more, about 25% w/w or more, about 30% w/w or more, about 35% w/w or more, about 40% w/w or more, about 45% w/w or more, about 50 w/w or more, about 55% w/w or more, about 60% w/w or more, about 65% w/w or more, about 70% w/w or more, about 75% w/w or more, about 80% w/w or more, about 85% w/w or more, about 90% w/w or more or about 95% w/w or more of an oil or an oily material and is still a solid material.

In one aspect, the present invention relates to a pharmaceutical composition in particulate form comprising tacrolimus and/or an analogue thereof together with one or more pharmaceutically acceptable excipient, wherein the composition upon oral administration to a mammal in need thereof exhibits an $AUC/AUC_{Prograf®}$ value of at least about 1.3, the AUC values being determined under similar conditions.

As it appears from the examples herein the bioavailability obtained after administration of a composition according to the invention is markedly improved. Thus, in specific embodiments, the $AUC/AUC_{Prograf®}$ value is at least about 1.5 such as about 1.75 or more, about 1.8 or more, about 1.9 or more, about 2.0 or more, about 2.5 or more, about 2.75 or more, about 3.0 or more, about 3.25 or more, about 3.5 or more, about 3.75 or more, about 4.0 or more, about 4.25 or more, about 4.5 or more, about 4.75 or more or about 5.0 or more, the AUC values being determined under similar conditions.

After oral administration of a pharmaceutical composition according to the present invention it is contemplated that the plasma concentration versus time profile show an extended period of time in which the plasma concentration is maintained within the therapeutic window (i.e. the plasma concentration leads to a therapeutic effect) without leading to serious unwanted side effects. Thus, a reduction in peak concentration may be observed. Accordingly, the invention relates to a pharmaceutical composition in particulate form comprising tacrolimus together with one or more pharmaceutically acceptable excipients, wherein the composition upon oral administration to a mammal in need thereof exhibits a $C_{max}$ that is at the most about 80% of that of $C_{max}$ for Prograf® tablets such as, e.g., at the most about 75%, at the most about 70%, at the most about 65%, at the most about 60%, at the most about 55%, at the most about 50%, at the most about 45% or at the most about 40%.

However, a reduction in peak concentration may not lead to a decrease in therapeutic effect as long as the plasma concentration of tacrolimus is maintained within the therapeutic window. Accordingly, the present invention also relates to a pharmaceutical composition, wherein $W_{50}$ is at least about 2 hours, such as, e.g., at least about 3 hours, at least about 4 hours, at least about 5 hours, at least about 6 hours, at least about 7 hours, at least about 8 hours, at least about 9 hours, about 10 hours or more, about 11 hours or more, about 12 hours or more, about 13 hours or about 14 hours or more.

Furthermore or moreover, a composition according to the invention has a $C_{diff}=[C_{max}-C_t(t=12 \text{ hours})]$ that is less than that of Prograf® under the same conditions. If $C_{diff}$ for Prograf® is set to 100 then $C_{diff}$ of a composition according to the invention is preferably 90 or less such as, e.g., about 85 or less, about 80 or less, about 75 or less, about 70 or less, about 65 or less, about 60 or less, about 55 or less, about 50 or less, about 45 or less or about 40 or less.

It is contemplated that the need for simultaneous food intake in order to secure a sufficient uptake of tacrolimus is significantly reduced or even completely abolished, when administering a pharmaceutical composition or dosage form of the present invention.

Thus, the pharmaceutical compositions of the invention provide significant higher bioavailability of tacrolimus, which may reduce the number of daily administered dosage units, and reduce or abolish the need for administration in connection with food intake, which provide for a higher degree of freedom for the recipient of the pharmaceutical compositions, and consequently the patients acceptance and/or compliance may be significantly improved. Furthermore, the compositions provide a significant reduction in side effects, especially side effect related to a high peak concentration (such as, e.g., nephro- and neuro-toxicity, diarrhea, constipation, abdominal pain, nausea etc) and provide for an extended release of tacrolimus leading to a better therapy.

One of the major challenges with respect to formulation of tacrolimus compositions is to avoid an adverse food effect. In general, tacrolimus is much better absorbed when it is administered orally without food. A great variation in bioavailability is therefore seen following administration with or without food. This dependency makes it difficult to give precise guidelines as to how large a dose that should be administered and, furthermore, it requires information to the patient about the dosing regime. The present invention aims at providing compositions wherein the adverse food effect is reduced. Thus, the present invention provides a composition, which does not exhibit a significant adverse food effect after administration of the composition to a mammal in need of such a treatment as evidenced by a value of $(AUC_{fed}/AUC_{fasted})$ of at least about 0.85 with a lower 90% confidence limit of at least 0.75.

More specifically, a pharmaceutical composition according to the invention has a value of $(AUC_{fed}/AUC_{fasted})$ of about 0.9 or more such as, e.g., about 0.95 or more, about 0.97 or more or about 1 or more such as, e.g., up to about 1.1 or up to about 1.2.

Apart from tacrolimus, the composition of the invention may also comprise a further therapeutically, prophylactically and/or diagnostically active substance. Notably combinations of tacrolimus with at least one of the following active substances are of interest: Substances that are indicated for use in connection with organ transplantation such as, e.g., steroids, calcineurin inhibitors and/or anti-proliferative agents. Specific examples include prednisone, prednisolone, methylprednisone, cyclosporin, mycophenolate, azathioprine, sirolimus, everolimus, mycophenolate sodium, and FTY720 (developed by the pharmaceutical company Novartis).

Dosage Forms

Useful dosage forms of the invention are solid oral dosage forms comprising the solid dispersion and/or solid solution and one or more pharmaceutically acceptable excipients, preferably unit dosage forms.

The pharmaceutical composition according to the invention is in particulate form and may be employed as such. However, in many cases it is more convenient to present the composition in the form of granules, pellets, microspheres, nanoparticles and the like or in the form of solid dosage forms including tablets, capsules and sachets and the like.

A solid dosage form according to the invention may be a single unit dosage form or it may in the form of a polydepot dosage form contain a multiplicity of individual units such as, e.g., pellets, beads and/or granules.

The dosage forms may further comprise pharmaceutically acceptable additives such as flavoring agents, coloring agents, taste-masking agents, pH-adjusting agents, buffering agents, preservatives, stabilizing agents, anti-oxidants, wetting agents, humidity-adjusting agents, surface-active agents, suspending agents, absorption enhancing agents and release modifying agents.

In a preferred embodiment, the dosage form comprises silica acid or a derivative or salt thereof including silicates, silicon dioxide and polymers thereof; and/or magnesium aluminosilicate and/or magnesium aluminometasilicate, bentonite, kaolin, magnesium trisilicate, montmorillonite and/or saponite. A particularly useful excipient to be included in the dosage forms is any silicon dioxide product having properties corresponding to Aeroperl® 300 (available from Degussa, Frankfurt, Germany).

A solid dosage form according to the present invention comprises a pharmaceutical composition in particulate form as described above. The details and particulars disclosed under this main aspect of the invention apply mutatis mutandis to the other aspects of the invention. Accordingly, the properties with respect to increase in bioavailability, changes in bioavailability parameters, reduction in adverse food effect as well as release of tacrolimus and/or an analogue thereof etc. described and/or claimed herein for pharmaceutical compositions in particulate form are analogues for a solid dosage form according to the present invention.

Normally, the concentration of the pharmaceutical composition in particulate form is in a range of from about 5 to 100% w/w such as, e.g., from about 10% to about 90% w/w, from about 15% to about 85% w/w, from about 20% to about 80% w/w, from about 25% to about 80% w/w, from about 30% to about 80% w/w, from about 35% to about 80% w/w, from about 40% to about 75% w/w, from about 45% to about 75% w/w or from about 50% to about 70% w/w of the dosage form. In an embodiment of the invention, the concentration of the pharmaceutical composition in particulate form is 50% w/w or more of the dosage form.

A solid dosage form according to the invention is obtained by processing the particulate material according to the invention by means of techniques well-known to a person skilled in the art. Normally, it involves further addition of one or more of the pharmaceutically acceptable excipients mentioned herein.

The composition or solid dosage form according to the invention may be designed to release tacrolimus and/or an analogue thereof in any suitable manner provided that the increase in bioavailability is present. Thus, the active substance may be released relatively fast in order to obtain an enhanced on-set of action, it may be released so as to follow zero or first order kinetics or it may be released in a modified manner in order to obtain a predetermined pattern of release. All of these ways are considered controlled manners. Plain formulations are also within the scope of the present invention.

The recommended dosage range for Prograf® is 0.1 to 0.2 mg/kg/day given every 12 hours in two divided doses. More importantly the blood levels has to be monitored. The typical level for 1-3 months is 7-20 ng/mL and 4-12 months the levels should be 5-15 ng/mL. This is only guiding values and may vary from types of transplant and ethnicity.

The following data have been found for kidney transplant patients:

|  | Caucasian n = 114 | | Black n = 56 | |
| --- | --- | --- | --- | --- |
| Time After Transplant | Dose (mg/kg) | Trough Concentrations (ng/mL) | Dose (mg/kg) | Trough Concentrations (ng/mL) |
| Day 7 | 0.18 | 12.0 | 0.23 | 10.9 |
| Month 1 | 0.17 | 12.8 | 0.26 | 12.9 |
| Month 6 | 0.14 | 11.8 | 0.24 | 11.5 |
| Month 12 | 0.13 | 10.1 | 0.19 | 11.0 |

The contemplated dosage recommendation for products of the present invention will be from 0.02 mg/kg/day to 0.15 mg/kg/day, dosed once a day.

Enteric Coatings—Delayed Release

It has been found that the efficacy of oral tacrolimus treatment can be greatly improved through proper design of the tacrolimus release profile. On the one hand relatively high doses of tacrolimus are required to avoid transplant rejection and on the other hand side effects often get too pronounced even at therapeutically relevant levels. Thus, the side effects such as acute nausea, vomiting, nephrotoxicity and neurotoxicity are directly linked to high peak plasma concentrations. This link has been demonstrated in dogs. In those cases where a lower dose has been used in order to avoid a high peak level, the dose-dependent side effects almost cease to occur at a certain threshold level and, if they occurred, they were much less pronounced. However, due to the decrease in dose (without increasing the bioavailability) the therapeutically effective level is only maintained for a short duration of time. The present invention addresses this problem by providing a pharmaceutical composition or dosage form containing tacrolimus, wherein the release of tacrolimus is designed to avoid high peak concentrations and at the same time, the composition is designed so that the overall bioavailability is maintained or increased as compared to commercially available tacrolimus-containing dosage forms. Moreover, by delaying the release of tacrolimus and at the same time provide a composition wherein tacrolimus is at least partly in dissolved form, it is possible to obtain a significant absorption in the distal part of the gastrointestinal tract.

Thus, the dosage form of the invention may further comprise one or more release modifying agents selected from the group consisting of water-miscible polymers, water-insoluble polymers, oils and oily materials.

The water-insoluble polymer may be ethyl cellulose, cellulose acetate, cellulose nitrate, and mixtures thereof. The water-miscible polymer may also be a cellulose derivative selected from the group consisting of hydroxypropyl methylcellulose (HPMC), hydroxypropyl cellulose (HPC), methylcellulose, sodium carboxymethylcellulose, hydroxyethyl cellulose, poloxamers, polyoxyethylene stearates, poly-ε-caprolactone, polyvinylpyrrolidone (PVP), polyvinylpyrrolidone-polyvinylacetate copolymer PVP-PVA, polymethacrylic polymers and polyvinyl alcohol (PVA), poly (ethylene oxide) (PEO) and mixtures thereof. Examples of especially useful polymethacrylic polymers are Eudragit® RS, Eudragit® RL, Eudragit® NE and Eudragit® E.

The oil or oily material may be hydrophilic and hydrophobic oils or oily materials.

Hydrophilic oil or oily material may be polyether glycols such as polypropylene glycols; polyoxyethylenes; polyoxypropylenes; poloxamers; polyglycolized glycerides such as Gelucire®, for example Gelucire® 50/13, Gelucire® 44/14, Gelucire® 50/10, Gelucire® 62/05 and mixtures thereof.

Hydrophobic oil or oily material may have a melting point of at least about 20° C. Useful examples are straight chain saturated hydrocarbons, sorbitan esters, paraffins; fats and oils such as cacao butter, beef tallow, lard, polyether glycol esters; higher fatty acid such as stearic acid, myristic acid, palmitic acid, higher alcohols such as cetanol, stearyl alcohol, low melting point waxes such as glyceryl monostearate, glyceryl monooleate, hydrogenated tallow, myristyl alcohol, stearyl alcohol, substituted and/or unsubstituted monoglycerides, substituted and/or unsubstituted diglycerides, substituted and/or unsubstituted triglycerides, yellow beeswax, white beeswax, carnauba wax, castor wax, japan wax, acetylate monoglycerides; NVP polymers, PVP polymers, acrylic polymers, and mixtures thereof.

The oil or oily-like material may also be a sorbitan ester such as, e.g., sorbitan di-isostearate, sorbitan dioleate, sorbitan monolaurate, sorbitan monoisostearate, sorbitan monooleate, sorbitan monopalmitate, sorbitan monostearate, sorbitan sesqui-isostearate, sorbitan sesquioleate, sorbitan sesquistearate, sorbitan tri-isostearate, sorbitan trioleate, sorbitan tristearate or mixtures thereof.

The oil or oily-like material may of course comprise a mixture of different oils or oily-like materials such as, e.g., a mixture of hydrophilic and/or hydrophobic materials.

Other suitable oils or oily-like materials may be solvents or semi-solid excipients like, e.g. propylene glycol, polyglycolised glycerides including Gelucire® 44/14, complex fatty materials of plant origin including theobroma oil, carnauba wax, vegetable oils like e.g. almond oil, coconut oil, corn oil, cottonseed oil, sesame oil, soya oil, olive oil, castor oil, palm kernels oil, peanut oil, rape oil, grape seed oil etc., hydrogenated vegetable oils such as, e.g. hydrogenated peanut oil, hydrogenated palm kernels oil, hydrogenated cottonseed oil, hydrogenated soya oil, hydrogenated castor oil, hydrogenated coconut oil; natural fatty materials of animal origin including beeswax, lanolin, fatty alcohols including cetyl, stearyl, lauric, myristic, palmitic, stearic fatty alcohols; esters including glycerol stearate, glycol stearate, ethyl oleate, isopropyl myristate; liquid interesterified semi-synthetic glycerides including Miglyol® 810/812; amide or fatty acid alcolamides including stearamide ethanol, diethanolamide of fatty coconut acids, acetic acid esters of mono and di-glycerides, citric acid esters of mono and di-glycerides, lactic acid esters of mono and diglycerides, mono and di-glycerides, poly-glycerol esters of fatty acids, poly-glycerol poly-ricinoleate, propylene glycol esters of fatty acids, sorbitan monostearates, sorbitan tristearates, sodium stearyl lactylates, calcium stearoyl lactylates, diacetyl tartaric acid esters of mono and di-glycerides etc.

A delayed release of active ingredient is desired in order to increase the bioavailability of active ingredient by delivering the ingredient in the gastrointestinal tract, i.e. the release predominantly takes place after passage of the stomach. For example, the dosage form of the present invention may be designed in order to release, after oral administration to a mammal in need thereof, at the most about 10 w/w %, preferably at the most about 7.5 w/w %, more preferably at the most about 5 w/w %, especially at the most about 2 w/w % of the total amount of active ingredient within the first 3 hours, preferably within 2 hours, more preferably within 1 hours, in particular within about 30 minutes after administration.

Further, the solid dosage form of the invention may, upon oral administration to a mammal in need thereof, release at least about 50 w/w % of the active ingredient within 24 hours, preferably within about 20 hours, more preferably within about 18 hours, especially within about 15 hours, in particular within about 12 hours.

Delayed release is mainly brought about by some kind of enteric coating. Whereas semipermeable coating will show some kind of delayed release, it may not preciously enough "delay" release. Additionally it requires a certain amount of time to release the content. The coating sought for this invention, is a pH dependant coating. This type of coating is very resistant to release of drug until a certain pH is reached. Within a small increment in the pH value, i.e. within an increase in pH of about 0.2 to 0.4, the film alters properties and becomes permeable.

Accordingly, the solid dosage forms of the invention may exhibit a delayed release of active ingredient by means of an enteric coating using a water-miscible polymer having a pH-dependant solubility in water. Examples of pH-sensitive polymers, which are relatively insoluble and impermeable at the pH of the stomach, but which are more soluble and permeable at the pH of the small intestine and colon include, but are not limited to, polyacrylamides; phthalate derivatives such as acid phthalates of carbohydrates including amylose acetate phthalate, cellulose acetate phthalate, cellulose acetate terephthalate, cellulose acetate isophthalate, other cellulose ester phthalates, cellulose ether phthalates, hydroxypropyl cellulose phthalate, hydroxypropylcellulose acetate phthalate, hydroxypropyl ethylcellulose phthalate, hydroxypropyl methylcellulose phthalate (HMPCP), methylcellulose phthalate, methyl cellulose acetate phthalate, polyvinyl acetate phthalate, polyvinyl acetate hydrogen phthalate, sodium cellulose acetate phthalate, starch acid phthalate; phthalates of other compounds including polyvinyl acetate phthalate (PVAP); other cellulose derivatives including hydroxypropyl methylcellulose acetate succinate (HPMCAS), carboxymethylcellulose, cellulose acetate trimellitate; alginates; carbomers; polyacrylic acid derivatives such as acrylic acid and acrylic ester copolymers, polymethacrylic acid and esters thereof, poly acrylic methacrylic acid copolymers, methacrylic acid copolymers (for example Eudragit® L and Eudragit® S); styrene-maleic acid dibutyl phthalate copolymer, styrene-maleic acid polyvinylacetate phthalate copolymer, styrene and maleic acid copolymers; shellac, starch glycolate; polacrylin; vinyl acetate and crotonic acid copolymers and mixtures thereof. pH-sensitive polymers of specific interest include shellac; phthalate derivatives, particularly cellulose acetate phthalate, polyvinylacetate phthalate, and hydroxypropylmethylcellulose phthalate; polyacrylic acid derivatives, particularly polymethyl methacrylate blended with acrylic acid and acrylic ester copolymers; and vinyl acetate and crotonic acid copolymers.

A first delayed release embodiment according to the invention is a "pH-dependent coated dosage form" such as, e.g., a tablet or a capsule. In the case of a tablet it comprises a tablet core comprising tacrolimus e.g. in a solid solution/dispersion as a multiparticulate product, a controlled release matrix of e.g. HPMC, a disintegrant, a lubricant, and one or more pharmaceutical carriers, such core being coated with a material, preferably a polymer, which is substantially insoluble and impermeable at the pH of the stomach, and which is more soluble and permeable at the pH of the small intestine. Preferably, the coating polymer is substantially insoluble and impermeable at pH<5.0, and water-soluble at pH>5.0. The tablet core may be coated with an amount of polymer sufficient to assure that substantially no release of tacrolimus from the dosage form occurs until the dosage form has exited the stomach and has resided in the small intestine for about 15 minutes or greater, preferably about 30 minutes or greater, thus assuring that minimal tacrolimus is released in the duodenum. Mixtures of a pH-sensitive polymer with a water-insoluble polymer may also be employed. Tablets are coated with an amount of polymer comprising from about 10% to about 80% of the weight of the tacrolimus-containing tablet core. Preferred tablets are coated with an amount of polymer comprising about 15% to about 50% of the weight of the tacrolimus tablet core.

pH-sensitive polymers which are very insoluble and impermeable at the pH of the stomach, but which are more soluble and permeable at the pH of the small intestine and colon include polyacrylamides, phthalate derivatives such as acid phthalates of carbohydrates, amylose acetate phthalate, cellulose acetate phthalate, other cellulose ester phthalates, cellulose ether phthalates, hydroxypropylcellulose phthalate, hydroxypropylethylcellulose phthalate, hydroxypropylmethylcellulose phthalate, methylcellulose phthalate, polyvinyl acetate phthalate, polyvinyl acetate hydrogen phthalate, sodium cellulose acetate phthalate, starch acid phthalate, styrene-maleic acid dibutyl phthalate copolymer, styrene-maleic acid polyvinylacetate phthalate copolymer, styrene and maleic acid copolymers, polyacrylic acid derivatives such as acrylic acid and acrylic ester copolymers, polymethacrylic acid and esters thereof, poly acrylic methacrylic acid copolymers, shellac, and vinyl acetate and crotonic acid copolymers.

Preferred pH-sensitive polymers include shellac; phthalate derivatives, particularly cellulose acetate phthalate, polyvinylacetate phthalate, and hydroxypropylmethylcellulose phthalate; polyacrylic acid derivatives, particularly polymethyl methacrylate blended with acrylic acid and acrylic ester copolymers; and vinyl acetate and crotonic acid copolymers.

The delay time before release of tacrolimus, after the "pH-dependent coated tablet" dosage form has exited the stomach, may be controlled by choice of the relative amounts of Eudragit-L® and Eudragit-S® in the coating, and by choice of the coating thickness. Eudragit-L® films dissolve above pH 6.0, and Eudragit-S® films dissolve above 7.0, and mixtures dissolve at an intermediate pH. Since the pH of the duodenum is approximately 6.0 and the pH of the colon is approximately 7.0, coatings composed of mixtures of Eudragit-L® and Eudragit-S® provide protection of the duodenum from tacrolimus. If it is desired to delay release of tacrolimus until the tacrolimus-containing "pH-dependent coated tablet" has reached the colon, Eudragit-S® may be used as the coating material, as described by Dew et al. (Br. J. Clin. Pharmac. 14 (1982) 405-408). In order to delay the release of tacrolimus for about 15 minutes or more, preferably 30 minutes or more, after the dosage form has exited the stomach, preferred coatings comprise from about 9:1 to about 1:9 Eudragit-L®/Eudragit-S®, more preferably from about 9:1 to about 1:4 Eudragit-L®/Eudragit-S®. The coating may comprise from about 3% to about 70% of the weight of the uncoated tablet core. Preferably, the coating comprises from about 5% to about 50% of the weight of the tablet core.

The release of the active substance from a composition having a delayed release coating could also be an enzymatic reaction, if for example Zein or mono/di-glyceride mixtures are employed as coating material.

Manufacture of the Compositions and Dosage Forms of the Invention

The present invention also provides a method for the preparation of the solid dispersion and/or solid solution of the invention, the method comprising the step of dispersing and/or dissolving tacrolimus or an analogue thereof in a hydrophilic or water-miscible vehicle to obtain a solid dispersion and/or solid solution at ambient temperature.

The pharmaceutical compositions of the invention may be prepared by any convenient method such as, e.g. granulation, mixing, spray drying etc. An example of a useful method is the controlled agglomeration method disclosed in WO 03/004001, i.e. a method enabling a controlled growth in particle size. The method involves spraying a first composition comprising an active ingredient and a melted vehicle onto a second solid carrier. Normally, the meltable vehicle has a melting point of at least 5° C., but the melting point is preferably below the melting point of tacrolimus. The melting point of the vehicle may be in the range of 10° C. to 150° C.

An advantage of using the controlled agglomeration method described in WO 03/004001 is that it is possible to apply a relatively large amount of a melt to a particulate material without having an undesirable growth in particle size.

The solid dispersion may also be obtained e.g. by employing organic solvents or by dispersing or dissolving the active substance in another suitable medium (e.g. an oil or an oily material that is in liquid form at room temperature or at elevated temperatures).

Solid dispersions (solvent method) are prepared by dissolving a physical mixture of the active substance (e.g. a drug substance) and the vehicle or carrier in a common organic solvent, followed by evaporation of the solvent. The vehicle carrier may be a hydrophilic polymer. Suitable organic solvents include pharmaceutical acceptable solvent in which the active substance is soluble such as methanol, ethanol, methylene chloride, chloroform, ethylacetate, acetone or mixtures thereof.

Suitable water soluble carriers include polymers such as polyethylene glycol, poloxamers, polyoxyethylene stearates, poly-s-caprolactone, polyvinylpyrrolidone (PVP), polyvinylpyrrolidone-polyvinylacetate copolymer PVP-PVA (Kollidon® VA64), poly-methacrylic polymers (Eudragit® RS, Eudragit® RL, Eudragit® NE, Eudragit® E) and polyvinyl alcohol (PVA), hydroxypropyl cellulose (HPC), hydroxypropyl methyl cellulose (HPMC), methyl cellulose, and poly (ethylene oxide) (PEO).

Polymers containing acidic functional groups may be suitable for solid dispersions, which release the active substance in a preferred pH range providing acceptable absorption in the intestines. Such polymers may be one ore more selected from the group comprising hydroxypropyl methylcellulose phthalate (HMPCP), polyvinyl acetate phthalate (PVAP), hydroxypropylmethylcellulose acetate succinate (HPMCAS), alginate, carbomer, carboxymethylcellulose, methacrylic acid copolymer (Eudragit L, Eudragit S), shellac, cellulose acetate phthalate (CAP), starch glycolate, polacrylin, methyl cellulose acetate phthalate, hydroxypropylcellulose acetate phthalate, cellulose acetate terephthalate, cellulose acetate isophthalate and cellulose acetate trimellitate.

In relations to amounts of the active substance and the polymer in the solid dispersion, the weight ratio of active substance to polymer may be in a range of from about 3:1 to about 1:20. However, narrower ranger of from about 3:1 to about 1:5, such as, e.g., from about 1:1 to about 1:3 or about may also be used.

The solid dispersion is preferably formed by spray drying techniques, controlled agglomeration, freeze-drying or coating on carrier particles or any other solvent removal process. The dried product contains the active substance present in the form of a solid dispersion including a molecular dispersion and a solid solution.

As an alternative to the use of organic solvents the drug and polymer may be co-grinded or extruded at elevated temperatures (melt extrusion).

The pharmaceutical compositions comprising tacrolimus at least partly in form of a solid dispersion or solution may in principle be prepared using any suitable procedure for preparing pharmaceutical compositions known within the art.

Apart from using the organic solvent based method, solid dispersion or solid solutions of tacrolimus and/or an analogue thereof may be obtained by dispersing and/or dissolving tacrolimus in the carrier composition used in the controlled agglomeration method. Stabilizing agents etc. may be added in order to ensure the stability of the solid dispersion/solution.

Uses

The solid dispersion and/or solution of the invention or the pharmaceutical composition of the invention may be used in the preparation of an solid oral dosage form such as tablets, capsules or sachets; or for the preparation of granules, pellets microspheres or nanoparticles.

Preferably, the solid dispersion or solid solution is used in the preparation of an immediate release solid dosage form or a delayed release solid dosage form.

Other uses of the solid dispersion or solid solution of the invention is for the preparation of a topical dosage form.

A further advantage of a composition of the present invention is the possibility of obtaining an effective therapeutic response with a decreased dosage compared to traditional oral treatment. Thus it is contemplated that the solid dosage form of the invention, when orally administered to a mammal in need thereof in a dose that is at the most about 85% w/w such as, e.g., at the most about 80% w/w, at the most about 75%, at the most about 70% w/w, at the most about 65% w/w, at the most about 60% w/w, at the most about 55% w/w or at the most about 50% w/w of the dose of tacrolimus administered in the form of Prograf® or a similar commercially available tacrolimus-containing product, is essentially bioequivalent with Prograf® or a similar commercially available tacrolimus-containing product.

Any of the tacrolimus-containing dosage forms, compositions, dispersions or solutions of the invention may improved treatment of conditions that respond to tacrolimus treatment.

Tacrolimus is indicated (or has been suggested) for the treatment of diseases such as, e.g., rejection reactions by transplantation of organs or tissues such as the heart, kidney, liver, bone marrow, skin, cornea, lung, pancreas, small intestine, limb, muscle, nerve, intervertebral disc, trachea, myoblast, cartilage, etc.; graft-versus-host reactions following bone marrow transplantation; autoimmune diseases such as rheumatoid arthritis, systemic lupus erythematosus, Hashimoto's thyroiditis, multiple sclerosis, myasthenia gravis, type I diabetes, etc.; infections caused by pathogenic microorganisms (e.g. *Aspergillus fumigatus, Fusarium oxysporum, Trichophyton asteroides*, etc.); inflammatory or hyperproliferative skin diseases or cutaneous manifestations of immunologically mediated diseases (e.g. psoriasis, atopic dermatitis, contact dermatitis, eczematoid dermatitis, seborrheic dermatitis, lichen planus, pemphigus, bullous pemphigoid, epidermolysis bullosa, urticaria, angioedema, vasculitides, erythema, dermal eosinophilia, lupus erythematosus, acne, and alopecia areata); autoimmune diseases of the eye (e.g. keratoconjunctivitis, vernal conjunctivitis, uveitis associated with Behcet's disease, keratitis, herpetic keratitis, conical keratitis, corneal epithelial dystrophy, keratoleukoma, ocular premphigus, Mooren's ulcer, scleritis, Graves' ophthalmopathy, Vogt-Koyanagi-Harada syndrome, keratoconjunctivitis sicca (dry eye), phlyctenule, iridocyclitis, sarcoidosis, endocrine ophthalmopathy, etc.); reversible obstructive airways diseases [asthma (e.g. bronchial asthma, allergic asthma, intrinsic asthma, extrinsic asthma, and dust asthma), particularly chronic or inveterate asthma (e.g. late asthma and airway hyper-responsiveness) bronchitis, etc.; mucosal or vascular inflammations (e.g. gastric ulcer, ischemic or thrombotic vascular injury, ischemic bowel diseases, enteritis, necrotizing enterocolitis, intestinal damages associated with thermal burns, leukotriene B4-mediated diseases); intestinal inflammations/allergies (e.g. coeliac diseases, proctitis, eosinophilic gastroenteritis, mastocytosis, Crohn's disease and ulcerative colitis); food-related allergic diseases with symptomatic manifestation remote from the gastrointestinal tract (e.g. migraine, rhinitis and eczema); renal diseases (e.g. intestitial nephritis, Goodpasture's syndrome, hemolytic uremic syndrome, and diabetic nephropathy); nervous diseases (e.g. multiple myositis, Guillain-Barre syndrome, Meniere's disease, multiple neuritis, solitary neuritis, cerebral infarction, Alzheimer's diseases Parkinson's diseases, amyotrophic lateral sclerosis (ALS) and radiculopathy); cerebral ischemic disease (e.g., head injury, hemorrhage in brain (e.g., subarachnoid hemorrhage, intracerebral hemorrhage), cerebral thrombosis, cerebral embolism, cardiac arrest, stroke, transient ischemic attack (TIA), hypertensive encephalopathy, cerebral infarction); endocrine diseases (e.g. hyperthyroidism, and Basedow's disease); hematic diseases (e.g. pure red cell aplasia, aplastic anemia, hypoplastic anemia, idiopathic thrombocytopenic purpura, autoimmune hemolytic anemia, agranulocytosis, pernicious anemia, megaloblastic anemia, and anerythroplasia); bone diseases (e.g. osteoporosis); respiratory diseases (e.g. sarcoidosis, pulmonary fibrosis, and idiopathic interstitial pneumonia); skin diseases (e.g. dermatomyositis, leukoderma vulgaris, ichthyosis vulgaris, photosensitivity, and cutaneous T-cell lymphoma); circulatory diseases (e.g. arteriosclerosis, atherosclerosis, aortitis syndrome, polyarteritis nodosa, and myocardosis); collagen diseases (e.g. scleroderma, Wegener's granuloma, and Sjogren's syndrome); adiposis; eosinophilic fasciitis; periodontal diseases (e.g. damage to gingiva, periodontium, alveolar bone or substantia ossea dentis); nephrotic syndrome (e.g. glomerulonephritis); male pattern alopecia, alopecia senile; muscular dystrophy; pyoderma and Sezary syndrome; chromosome abnormality-associated diseases (e.g. Down's syndrome); Addison's disease; active oxygen-mediated diseases [e.g. organ injury (e.g. ischemic circulation disorders of organs (e.g. heart, liver, kidney, digestive tract, etc.) associated with preservation, transplantation, or ischemic diseases (e.g. thrombosis, cardial infarction, etc.)); intestinal diseases (e.g. endotoxin shock, pseudomembranous colitis, and drug- or radiation-induced colitis); renal diseases (e.g. ischemic acute renal insufficiency, chronic renal failure); pulmonary diseases (e.g. toxicosis caused by pulmonary oxygen or drugs (e.g. paracort, bleomycin, etc.), lung cancer, and pulmonary emphysema); ocular diseases (e.g. cataracta, iron-storage disease (siderosis bulbi), retinitis, pigmentosa, senile plaques, vitreous scarring, corneal alkali burn); dermatitis (e.g. erythema multiforme, linear immunoglobulin A bullous dermatitis, cement dermatitis); and other diseases (e.g. gingivitis, periodontitis, sepsis, pancreatitis, and diseases caused by environmental pollution (e.g. air pollution), aging, carcinogen, metastasis of carcinoma, and hypobaropathy)]; diseases caused by histamine release or leukotriene C4 release; restenosis of coronary artery following angioplasty and prevention of postsurgical adhesions; autoimmune diseases and inflammatory conditions (e.g., primary mucosal edema, autoimmune atrophic gastritis, premature menopause, male sterility, juvenile diabetes mellitus, pemphigus vulgaris, pemphigoid, sympathetic ophthalmitis, lens-induced uveitis, idiopathic leukopenia, active chronic hepatitis, idiopathic cirrhosis, discoid lupus erythematosus, autoimmune orchitis, arthritis (e.g. arthritis deformans), or polychondritis); Human Immunodeficiency Virus (HIV) infection, AIDS; allergic conjunctivitis; hypertrophic cicatrix and keloid due to trauma, burn, or surgery.

In addition, tricyclic macrolides like e.g. tacrolimus have liver regenerating activity and/or activities of stimulating hypertrophy and hyperplasia of hepatocytes. Therefore, the pharmaceutical composition of the present invention is useful for increasing the effect of the therapy and/or prophylaxis of liver diseases [e.g. immunogenic diseases (e.g. chronic autoimmune liver diseases such as autoimmune hepatic diseases, primary biliary cirrhosis or sclerosing cholangitis), partial liver resection, acute liver necrosis (e.g. necrosis caused by toxins, viral hepatitis, shock, or anoxia), hepatitis B, non-A non-B hepatitis, hepatocirrhosis, and hepatic failure (e.g. fulminant hepatitis, late-onset hepatitis and "acute-on-chronic" liver failure (acute liver failure on chronic liver diseases))].

Furthermore, a composition of the present invention is useful for increasing the effect of the prevention and/or treatment of various diseases because of the useful pharmacological activity of the tricyclic macrolides, such as augmenting activity of chemotherapeutic effect, activity of cytomegalovirus infection, anti-inflammatory activity, inhibiting activity against peptidyl-prolyl isomerase or rotamase, antimalarial activity, antitumor activity and so on.

Materials and Methods

Materials

Tacrolimus (supplied by Eurotrade); batch no RD 03-111
Lactose monohydrate 200 mesh (from DMV)
Granulated silicium oxide, Aeroperl® 300, (Degussa)
Polyethylene glycol 6000, Pluracol® E6000 (from BASF)
Poloxamer 188, Pluronic® F-68 (from BASF)
Glyceryl monostearate, Rylo® MD50, (from Danisco Cultor), grade Ph. Eur.; batch no. 4010056276
Avicel PH200 (microcrystalline cellulose) (from FMC)
Lactose DCL 11 (from DMV)
Magnesium stearate
Croscarmellose sodium, Ac-Di-Sol® (from FMC)
Eudragit® L30D.55 (from Degussa); batch no. 1220314079
Triethyl citrate (from Merck); batch no. RD03-122
Anti-foam emulsion (from Unikem)
Micro talc Either tablets, capsules or granules might be enteric coated with different types of polymers such as hydroxypropylmethylcellulose acetate succinate (Aqoat), cellulose acetate phthalate CAP, hydroxypropylmethylcellulose phthalate HPMCP or methacrylic acid copolymers such as Eudragit® L30D, Eudragit® 100/S, Eudragit® 100/L.

Comparison prior art tacrolimus formulation for in vivo studies:

Prograf® Hard Gelatin Capsules, manufactured by Fujisawa Ireland Ltd.

| Ingredients | mg |
|---|---|
| Tacrolimus, anhydr. | 1.0 |
| Gelatin | 6.9 |
| Hypromellose | 1.0 |
| Lactose monohydrate | 24.7 |
| Magnesium stearate | 0.3 |
| Shellac | q.s. |
| Soybean lecitine | q.s. |
| Iron oxide red (E172) | q.s. |
| Titanium dioxide (E171) | q.s. |
| Dimeticone (E900) | q.s. |

Methods

Determination of Weight Variation

The tablets prepared in the Examples herein were subjected to a test for weight variation performed in accordance with Ph. Eur.

Determination of Average Tablet Hardness

The tablets prepared in the Examples herein were subjected to at test for tablet hardness employing Schleuniger Model 6D apparatus and performed in accordance with the general instructions for the apparatus.

Determination of Disintegration Time

The time for a tablet to disintegrate, i.e. to decompose into particles or agglomerates, was determined in accordance with Ph. Eur.

Determination of Geometric Weight Mean Diameter $d_{gw}$

The geometric weight mean diameter was determined by employment of a method of laser diffraction dispersing the particulate material obtained (or the starting material) in air. The measurements were performed at 1 bar dispersive pressure in Sympatec Helos equipment, which records the distribution of the equivalent spherical diameter. This distribution is fitted to a log normal volume-size distribution.

When used herein, "geometric weight mean diameter" means the mean diameter of the log normal volume-size distribution.

In Vitro Dissolution Tests

The following test methods were applies to the compositions and dosage forms of the present invention.

Test 1:

In vitro dissolution test according to USP Method A, delayed release articles (USP paddle method; rotation speed: 50 rpm; 37° C.; after 2 hours in acidic medium, the medium is changed to phosphate buffer pH 6.8).

Test 2:

In vitro dissolution test in aqueous dissolution medium adjusted to pH 4.5 (900 ml water with 0.005% HPC (hydroxypropylcellulose) adjusted to pH 4.5; 37° C.; USP Paddle method; rotation speed: 50 rpm).

In Vivo Studies in Beagle Dogs

In vivo studies with the purpose of determining the bioavailability of the compositions of the present invention relative to the bioavailability of the commercially available tacrolimus product, i.e. Prograf®, was performed using Beagle dogs.

The experimental work was performed in Denmark using male Beagle dogs each having a body weight of 12-18 kg (starting weight). The studies were conducted as open, non-randomised, cross-over studies. The dogs were premedicated with Primperan inj. 5 mg/ml (anti-emetica) and an oral dose of 0.5 to 4 mg of tacrolimus was administered. The dogs were fasted for 10 hours prior to dosing (water ad libitum) and were fed 5 hours after dosing (water ad libitum). Each dog was dosed with the specified dose of tacrolimus without taking the weight of the dog into consideration.

Blood samples were collected at vena jugularis externa at the following points of time: Pre-dose, 1, 1.5, 2, 3, 4, 6, 8, 12 and 24 hours after dosing. 4 ml of blood were collected, mixed with EDTA, and the samples were frozen (−80° C.). The blood samples were analyzed using on-line extraction LC/MS and results were given in ng/mL.

The determined full blood concentration profiles of tacrolimus were treated using the Pharmacokinetic softwear WinNonlin®, (Pharsight, Calif.; USA) to calculate the pharmacokinetic parameters. All data are dose adjusted.

The following examples serve the purpose of illustration of the invention and are not intended to limiting the scope of the present invention.

Pharmaceutical compositions and dosage forms of the invention are exemplified in examples 1-4 including results of in vitro dissolution tests. Results of in vivo comparison studies in Beagle dogs (blood plasma concentration) are found in examples 5-6.

EXAMPLE 1

Immediate Release Tablet with Improved Bioavailability

Tablet Composition:

| | % | mg |
|---|---|---|
| Tacrolimus | 0.50 | 1.00 |
| Lactose 200 mesh | 49.75 | 100.00 |
| PEG 6000 | 34.48 | 69.30 |

-continued

|  | % | mg |
|---|---|---|
| Poloxamer 188 | 14.78 | 29.70 |
| Magnesium stearate | 0.50 | 1.01 |
| Total | 100.00 | 201.01 |

Tacrolimus was dissolved in polyethylene glycol 6000 and poloxamer 188 (in a 70:30 w/w ratio) at 70° C. The solution was sprayed onto 250 g lactose in a fluid bed Strea-1. The granular product was sifted through sieve no. 0.7 mm and blended with magnesium stearate for 0.5 minutes in a Turbula mixer. The mixture was compressed into 8 mm tablets of 1 mg active ingredient (200 mg tablet) with compound cup shaped.

Mean disintegration time: 20 minutes. Hardness: 45 N.

EXAMPLE 2

Immediate Release Tablet Based on PEG 6000/Poloxamer 188

Tablet Composition:

| Substance | % | mg |
|---|---|---|
| Tacrolimus | 1.98 | 2.00 |
| Lactose monohydrate, Lactose 200 mesh | 40.50 | 40.91 |
| PEG 6000 | 33.26 | 33.60 |
| Poloxamer 188, Lutrol 68 | 14.40 | 14.40 |
| Magnesium Stearate | 0.50 | 0.51 |
| Talc | 4.50 | 4.55 |
| Croscarmellose sodium, Ac-Di-Sol | 5.00 | 5.05 |
|  | 100.00 | 101.01 |

Tacrolimus was dissolved in PEG 6000 at a temperature above 80° C. Poloxamer 188 was added and the solution was heated to a temperature above 80° C. Using feed unit Phast FS1.7, the solution was sprayed onto 200 g lactose monohydrate in a fluid bed Phast FB100. The resulting granulate was passed through a Comill, sieve no. 1397, 4500 rpm, and blended with croscarmellose sodium for 3 minutes in a Turbula mixer.

Magnesium stearate and talc was sifted through sieve no. 300 and mixed in a Turbola mixer for 3 min. The granulate was mixed with the magnesium stearate:talc (1:9) for 0.5 minutes in a Turbula mixer.

The resulting mixture was compressed into 6 mm tablets of 2 mg active ingredient (100 mg tablet) with compound cup shape.

Mean disintegration time: 7 minutes. Hardness: 65 N

The tablets were subjected to an in vitro dissolution test in dissolution medium: 900 ml, aqueous medium with 0.005% HPC (hydroxypropylcellulose) adjusted to pH=4.5, USP paddle method; rotation speed: 50 rpm; and the following dissolution profile was found:

| Time (minutes) | % release | Rsd % |
|---|---|---|
| 0 | 0 | 0 |
| 5 | 27.2 | 15.1 |
| 10 | 49.1 | 10.9 |
| 20 | 80.7 | 8.0 |
| 35 | 98.9 | 5.4 |
| 42 | 102.7 | 3.6 |
| 52 | 104.9 | 2.0 |

EXAMPLE 3

Enteric Coating of Immediate Release Tablets of Example 2

The enteric coating is based on the acrylic polymer Eudragit® L30D-55. Eudragit® L30D is supplied as an aqueous latex suspension creating a water insoluble film when the water is evaporated during coating. The polymer is insoluble at pH-values below 5.0 and readily soluble at pH-values above 6.0. The tablets prepared as described in example 2 were coated with the following film coating composition:

| Substance | w/w % |
|---|---|
| Eudragit ® L30D-55 | 40 |
| Water | 52 |
| Triethyl citrate | 1.8 |
| Anti-foam emulsion | 0.2 |
| Talc (micro) | 6 |
| Total | 100 |

The amount of applied film polymer (Eudragit®) is based on a calculation of mg filmpolymer per cm2 of tablet surface. The thickness of the enteric coating was 80 p. m. A verification of the film-thickness applied was based on measuring the increase in tablet height with a digital micrometer. The film coating process was performed in a Phast FB100 fluid bed equipped with a Wurster like insert using an inlet air temperature of 50° C., inlet air flow of 100 cbm per hour, product temperature of 38° C. and feed rate 15 g/min.

The coated tablets were cured in an oven at 30° C. for 48 hours. Alternatively, the coated tablets may more efficiently be cured at 40° C. for 24 hours.

The enteric coated tablets were subjected to in vitro dissolution tests using two different dissolution media/tests.

Using the dissolution medium/test: 900 ml aqueous medium with 0.005% HPC (hydroxypropylcellulose) adjusted to pH=4.5 (USP paddle method; rotation speed: 50 rpm), the following dissolution profile was found:

| Time (hours) | % release | Rsd % |
|---|---|---|
| 0 | 0 | 0 |
| 4 | 0.8 | 32.3 |
| 8 | 0.4 | 61.1 |
| 15 | 11.0 | 17.3 |
| 17 | 13.2 | 12.1 |

Using the dissolution medium/test: USP Method A, delayed release articles (USP paddle method; rotation speed: 50 rpm), the following dissolution profile was found:

| Time (minutes) | % release | Rsd % |
|---|---|---|
| 0 | 0 | NA |
| 120 | 0 | NA |
| 155 | 84.8 | 12.8 |
| 165 | 102.9 | NA |
| 175 | 101.0 | 3.5 |

EXAMPLE 4

The following tacrolimus formulation was prepared as described in example 2:

| Substance | % | mg |
|---|---|---|
| Tacrolimus | 2.09 | 2.10 |
| Lactose monohydrate, 200 mesh | 42.75 | 42.95 |
| PEG 6000 | 35.11 | 35.28 |
| Poloxamer 188, Lutrol 68 | 15.05 | 15.12 |
| Magnesium stearate | 0.50 | 0.50 |
| Talc | 4.50 | 4.52 |
| | 100.00 | 100.48 |

The mixture was compressed into 6 mm tablets of 2.1 mg active ingredient (100 mg tablet with compound cup shape). Average tablet hardness: 41N.

EXAMPLE 5

In Vivo Test of Immediate Release Formulations in Dogs

The following tacrolimus formulation was prepared as described in example 2:

| Substance | % | mg |
|---|---|---|
| Tacrolimus | 0.76 | 0.5 |
| Lactose 200 mesh | 49.14 | 32.43 |
| PEG 6000 | 34.73 | 22.92 |
| Poloxamer 188 | 14.88 | 9.82 |
| magnesium stearate | 0.50 | 0.33 |
| Total | 100.00 | 66.00 |

66 mg of the granulate was weighed into hard gelatine capsules.

An in vivo study of this formulation 0.5 mg in a Beagle dog, performed as described above under Methods, relative to Prograf®, 4×1 mg (Batch no.: 1C56050), gave the following results:
Blood concentrations (ng/mL) in dog no. F1182, after administration of formulation:

| | Formulation | |
|---|---|---|
| Time (hr) | Prograf (4 mg) | Invention Dose adj. to 4 mg |
| 0 | 0 | 0.0 |
| 0.5 | 0.5 | 10.5 |
| 1.0 | 5.5 | 44.1 |
| 1.5 | 4.1 | 34.3 |
| 2.0 | 4.0 | 21.0 |
| 3.0 | 4.6 | 10.5 |
| 4.0 | 4.0 | 9.1 |
| 6.0 | 2.7 | 4.9 |
| 8.0 | 2.0 | 4.2 |
| 12.0 | 2.0 | 3.5 |
| 24.0 | 0.7 | 2.1 |

Relative bioavailability based on AUC (invention/Prograf): 293%.

EXAMPLE 6

In Vivo Test of Immediate Release Formulations in Dogs

The following tacrolimus formulation of the invention was prepared as described in example 2:

| Substance | % | mg |
|---|---|---|
| Tacrolimus | 1.86 | 0.50 |
| Lactose monohydrate, Lactose 200 mesh | 43.56 | 11.72 |
| PEG 6000 | 31.21 | 8.40 |
| Poloxamer 188, Lutrol 68 | 13.37 | 3.60 |
| Magnesium Stearate | 0.50 | 0.13 |
| Talc | 4.50 | 1.21 |
| Croscarmellose sodium, Ac-Di-Sol | 5.00 | 1.35 |
| | 100.00 | 26.92 |

This was compressed into 4 mm tablets of 0.5 mg active ingredient (27 mg tablet with compound cup shape).

An in vivo study of this formulation 0.5 mg in a Beagle dog, performed as described above under Methods, relative to Prograf®, 0.5 mg capsules (Batch no.: OC512OD), gave the following results:
Blood concentrations (ng/mL) in dog no. 1, after administration of formulation:

| | Formulation | |
|---|---|---|
| Time (hr) | Prograf (0.5 mg) | Formulation B (0.5 mg) |
| 0 | 0 | 0 |
| 0.5 | 0.95 | 0.04 |
| 1.0 | 0.84 | 1.56 |
| 1.5 | 0.55 | 4.68 |
| 2.0 | 0.40 | 9.11 |
| 3.0 | 0.26 | 2.82 |
| 4.0 | 0.18 | 2.46 |
| 6.0 | 0.18 | 1.10 |
| 8.0 | 0.14 | 1.25 |
| 12.0 | 0.11 | 0.74 |
| 24.0 | 0.06 | 0.40 |
| 25.0 | 0.06 | 0.44 |

Relative bioavailability based on AUC (invention vs. Prograf®): 742%

The invention claimed is:

1. A solid pharmaceutical composition comprising tacrolimus containing particles, wherein the particles comprise (i) tacrolimus in polyethylene glycol having an average molecular weight of at least 1500 and a poloxamer, and (ii) a solid carrier, wherein the tacrolimus is present in the composition at a concentration of between 0.01 w/w % and 15 w/w %.

2. The solid pharmaceutical composition according to claim 1, wherein the tacrolimus is partly dissolved in the polyethylene glycol and the poloxamer to form a mixture of solid dispersion and solid solution at ambient temperature.

3. The solid pharmaceutical composition according to claim 1, wherein the tacrolimus is fully dissolved in the polyethylene glycol and the poloxamer to form a solid solution at ambient temperature.

4. The solid pharmaceutical composition according to claim 1, wherein the polyethylene glycol and the poloxamer have a melting point of at least 30° C.

5. The solid pharmaceutical composition according to claim 1, wherein the concentration of tacrolimus in the polyethylene glycol and poloxamer is at the most 10 w/w %.

6. The solid pharmaceutical composition according to claim 1, wherein the concentration of tacrolimus in the polyethylene glycol and poloxamer is at least 0.05 w/w %.

7. The solid pharmaceutical composition according to claim 1, wherein at least 50 w/w % of the tacrolimus is released within 30 minutes, when tested in any dissolution test according to USP using an aqueous dissolution medium.

8. The solid pharmaceutical composition according to claim 1, wherein at least 75 w/w % of the tacrolimus is released within 40 minutes, when tested in any dissolution test according to USP using an aqueous dissolution medium.

9. The solid pharmaceutical composition according to claim 1, wherein at least 90 w/w % of the tacrolimus is released within 60 minutes, when tested in any dissolution test according to USP using an aqueous dissolution medium.

10. The solid pharmaceutical composition according to claim 1, wherein the mixture comprises a polyethylene glycol and a poloxamer in a proportion of between 1:3 and 10:1.

11. The solid pharmaceutical composition according to claim 10, wherein the poloxamer is poloxamer 188.

12. The solid pharmaceutical composition according to claim 10, wherein the polyethylene glycol has an average molecular weight of about 6000 (PEG6000).

13. The solid pharmaceutical composition according to claim 1, comprising one or more pharmaceutically acceptable excipients.

14. The solid pharmaceutical composition according to claim 13, wherein the pharmaceutically acceptable excipients are selected from the group consisting of fillers, disintegrants, binders and lubricants.

15. The solid pharmaceutical composition according to claim 1, wherein the particles have a geometric weight mean diameter $d_{gw}$ from 10 μm to 2000 μm.

16. The solid pharmaceutical composition according to claim 1, wherein the particles have a geometric weight mean diameter $d_{gw}$ from 50 μm to 300 μm.

17. A solid dosage form comprising the solid pharmaceutical composition according to claim 13, which is a solid oral dosage form.

18. The solid dosage form according to claim 17, which is a unit dosage form.

19. The solid dosage form according to claim 17, which further comprises a pharmaceutically acceptable additive selected from the group consisting of flavoring agents, coloring agents, taste-masking agents, pH-adjusting agents, buffering agents, preservatives, stabilizing agents, anti-oxidants, wetting agents, humidity-adjusting agents, surface-active agents, suspending agents, absorption enhancing agents and release modifying agents.

20. The solid dosage form according to claim 17, wherein at least one pharmaceutical acceptable excipient is selected from the group consisting of silica acid or salt thereof.

21. The solid dosage form according to claim 17, wherein at least one pharmaceutically acceptable excipient is a silica acid or salt thereof.

22. The solid dosage form according to claim 17, wherein at least one pharmaceutical acceptable excipient is silicon dioxide or a polymer thereof.

23. The solid dosage form according to claim 19 comprising one or more release modifying agents selected from the group consisting of water-miscible polymers, water-insoluble polymers, oils and oily materials.

24. The solid dosage form according to claim 23, wherein the water-insoluble polymer is selected from the group consisting of ethyl cellulose, cellulose acetate, cellulose nitrate, and mixtures thereof.

25. The solid dosage form according to claim 23, wherein the oil or oily material is selected from the group consisting of hydrophilic and hydrophobic oils or oily materials.

26. The solid dosage form according to claim 23, wherein the oil or oily material is hydrophilic and selected from the group consisting of polyether glycols and mixtures thereof.

27. The solid dosage form according to claim 23, wherein the oil or oily material is hydrophobic and selected from the group consisting of straight chain saturated hydrocarbons, sorbitan esters, paraffins; fats and oils; higher fatty acid, stearic acid, myristic acid, palmitic acid, higher alcohols, low melting point waxes, yellow beeswax, white beeswax, carnauba wax, castor wax, japan wax, acetate monoglycerides; NVP polymers, PVP polymers, acrylic polymers, and mixtures thereof.

28. The solid dosage form according to claim 27, wherein the oil or oily hydrophobic material has a melting point of at least 20° C.

29. The solid dosage form according to claim 23, wherein the water-miscible polymer is a cellulose derivative selected from the group consisting of hydroxypropyl methylcellulose (HPMC), hydroxypropyl cellulose (HPC), methylcellulose, sodium carboxymethylcellulose, hydroxyethyl cellulose, poloxamers, polyoxyethylene stearates, poly-s-caprolactone, polyvinylpyrrolidone (PVP), polyvinylpyrrolidone-polyvinylacetate copolymer PVP-PVA, polymethacrylic polymers and polyvinyl alcohol (PVA), poly (ethylene oxide) (PEO) and mixtures thereof.

30. The solid dosage form according to claim 29, wherein the polymethacrylic polymers are selected among Eudragit® RS, Eudragit® RL, Eudragit® NE and Eudragit® E.

31. The solid dosage form according to claim 23, which is entero-coated using a water-miscible polymer having a pH-dependant solubility in water.

32. The solid dosage form according to claim 31, wherein the water-miscible polymer is selected from the group consisting of polyacrylamides; cellulose acetate phthalate, cellulose acetate terephthalate, cellulose acetate isophthalate, cellulose ester phthalates, cellulose ether phthalates, hydroxypropyl cellulose phthalate, hydroxypropylcellulose acetate phthalate, hydroxypropyl ethylcellulose phthalate, hydroxypropyl methylcellulose phthalate (HMPCP), methylcellulose phthalate, methyl cellulose acetate phthalate, polyvinyl acetate phthalate, polyvinyl acetate hydrogen phthalate, sodium cellulose acetate phthalate, starch acid phthalate; polyvinyl acetate phthalate (PVAP); hydroxypropyl methylcellulose acetate succinate (HPMCAS), carboxymethylcellulose, cellulose acetate trimellitate; alginates; carbomers; polyacrylic acid derivatives, polymethacrylic acid and esters thereof, poly acrylic methacrylic acid copolymers, methacrylic acid copolymers, styrene-maleic acid dibutyl phthalate copolymer, styrene-maleic acid polyvinylacetate phthalate copolymer, styrene and maleic acid copolymers; shellac, starch glycolat; polacrylin; vinyl acetate and crotonic acid copolymers and mixtures thereof.

33. The solid dosage form according to claim 31, which upon oral administration to a mammal in need thereof releases at the most about 10% w/w of the tacrolimus within the first 3 hours following administration.

34. The solid dosage form according to claim 17, wherein the solid dosage form upon oral administration to a mammal in need thereof provides an AUC or $C_{max}$ of tacrolimus that is 80%-125% of that provided by a capsule dosage form approved under U.S. Food and Drug Administration NDA No. 050708, wherein the dose of tacrolimus administered with the solid dosage form is at the most about 85% w/w of the dose of tacrolimus administered in the form of the capsule dosage form approved under NDA No. 050708.

35. The solid dosage form according to claim 17, wherein the solid dosage form upon oral administration to a mammal in need thereof releases at least 50% w/w of the tacrolimus within 24 hours.

36. A method for the preparation of the solid pharmaceutical composition according to claim 1, the method comprising the steps of (a) dispersing and/or dissolving tacrolimus in a polyethylene glycol having an average molecular weight of at least 1500 and a poloxamer to form a mixture, and (b) spraying the mixture onto a solid carrier to obtain the solid pharmaceutical composition.

37. The method according to claim 36, wherein step (a) is performed in the absence of an organic solvent.

38. A solid pharmaceutical composition prepared according to the method of claim 36.

39. A solid pharmaceutical composition prepared according to the method of claim 37.

40. The solid pharmaceutical composition according to claim 1, wherein the solid pharmaceutical composition is a tablet.

41. A solid pharmaceutical composition comprising tacrolimus dispersed or dissolved, in the absence of an organic solvent, in polyethylene glycol having an average molecular weight of at least 1500 and a poloxamer, wherein the tacrolimus is present therein in a concentration of between about 0.01 w/w % and about 15 w/w %, wherein the solid pharmaceutical is in particulate form.

42. The solid dosage form according to claim 23, wherein the release modifying agent is hydroxypropyl methylcellulose (HPMC).

43. A solid pharmaceutical composition comprising agglomerated particles comprising a solid carrier and tacrolimus dispersed or dissolved in polyethylene glycol having an average molecular weight of at least 1500 and a poloxamer, wherein
  (i) the tacrolimus is present in the composition at a concentration of between about 0.01 w/w % and about 15 w/w %,
  (ii) the particles have a geometric weight mean diameter $d_{gw}$ of from 100 to 1000 μm, and
  (iii) the weight ratio of polyethylene glycol to poloxamer is between 1:3 and 10:1.

44. A solid pharmaceutical composition prepared by
  (a) spraying a solid carrier with tacrolimus dispersed or dissolved in polyethylene glycol having an average molecular weight of 1500 to 8000 and a poloxamer,
  (b) mechanically working the product from step (a) to form agglomerated particles having a geometric weight mean diameter $d_{gw}$ of from 100 to 1000 μm, and
  (c) compressing the agglomerated particles,
wherein
  (i) the tacrolimus is present in the composition at a concentration of between about 0.01 w/w % and about 15 w/w %, and
  (ii) the weight ratio of polyethylene glycol to poloxamer is between 1:3 and 10:1.

45. The solid pharmaceutical composition according to claim 44, wherein step (c) comprises compressing the agglomerated particles into a tablet.

* * * * *